(12) United States Patent
Arai et al.

(10) Patent No.: US 7,534,105 B2
(45) Date of Patent: May 19, 2009

(54) OCCLUDATOR, FACE BOW, OCCLUSION-CONFIRMING SYSTEM AND TEMPOROMANDIBULAR JOINT-REPRODUCING SYSTEM

(75) Inventors: Yoshinori Arai, Tokyo (JP); Yutaka Akiyama, Tokyo (JP); Toru Ishizuka, Tokyo (JP); Hitoshi Tsunashima, Tokyo (JP); Ayuta Yamada, Tokyo (JP)

(73) Assignee: Nihon University, Tokyo (JP)

( * ) Notice: Subject to any disclaimer, the term of this patent is extended or adjusted under 35 U.S.C. 154(b) by 628 days.

(21) Appl. No.: 10/529,100

(22) PCT Filed: Sep. 26, 2003

(86) PCT No.: PCT/JP03/12345

§ 371 (c)(1),
(2), (4) Date: Mar. 24, 2005

(87) PCT Pub. No.: WO2004/028396

PCT Pub. Date: Apr. 8, 2004

(65) Prior Publication Data

US 2005/0277086 A1 Dec. 15, 2005

(30) Foreign Application Priority Data

Sep. 27, 2002 (JP) ............................. 2002-283250

(51) Int. Cl.
*A61C 11/00* (2006.01)
*A61C 19/04* (2006.01)
(52) U.S. Cl. .......................................... 433/57; 433/64
(58) Field of Classification Search .................. 433/54, 433/57, 58, 59, 61, 62, 64
See application file for complete search history.

(56) References Cited

U.S. PATENT DOCUMENTS 4,084,319 A 4/1978 Dragan
(Continued)

FOREIGN PATENT DOCUMENTS

EP 0 590 208 A2 4/1994
(Continued)

OTHER PUBLICATIONS

International Search Report dated Dec. 24, 2003.
(Continued)

*Primary Examiner*—Ralph A Lewis
(74) *Attorney, Agent, or Firm*—Young Basile Nanion MacFarlane & Helmholdt, P.C.

(57) ABSTRACT

It is intended to provide an occludator whereby joint movements at occlusion being similar to the actual temporomandibular joint movements of an individual patient or ideal movements can be reproduced, and a face bow to be used for the occludator. To achieve this object, an occlusion plane against a standard plane is accurately drawn by using the above face bow F whereby the occlusion plane can be drawn at a high accuracy. A solid model of the tempromandibular joint similar to the tempromandibular joint form of an actual patient is used as the joint unit of the occludator K, while the positional relationship in the body at occlusion is three-dimensionally reproduced in the occludator I with the use of the above-described face bow F. It is also intended to provide an occlusion-confirming system and a tempromandibular joint-reproducing system with the use of an occludator whereby joint movements at occlusion being similar to the actual tempromandibular joint movements of an individual patient or ideal movements can be reproduced. To achieve this object, the tempromandibular joint of the body is photographed with a local X-ray CT device to give three-dimensional image data and then a solid model of the tempromandibular joint is constructed based on the three-dimensional image data. This solid model is employed as the joint unit of the occludator K and the positional relationship in the body at occlusion is three-dimensionally reproduced.

26 Claims, 30 Drawing Sheets

U.S. PATENT DOCUMENTS

| | | | | |
|---|---|---|---|---|
| 4,509,919 | A | * | 4/1985 | Gerbellot-Barrillon ....... 433/57 |
| 5,160,262 | A | * | 11/1992 | Alpern et al. .................. 433/58 |
| 5,176,515 | A | * | 1/1993 | Andrews ..................... 433/24 |
| 5,338,193 | A | * | 8/1994 | Mack .......................... 433/57 |
| 5,494,440 | A | | 2/1996 | Silva et al. |
| 6,210,162 | B1 | * | 4/2001 | Chishti et al. ............... 433/213 |
| 6,287,113 | B1 | * | 9/2001 | Nagata ........................ 433/57 |
| 2002/0012896 | A1 | * | 1/2002 | Nagata ........................ 433/57 |
| 2007/0207441 | A1 | * | 9/2007 | Lauren ....................... 433/213 |

FOREIGN PATENT DOCUMENTS

| | | | |
|---|---|---|---|
| JP | | 417034 B1 | 4/1966 |
| JP | | 4116670 B1 | 9/1966 |
| JP | | 4810869 B1 | 4/1973 |
| JP | | 09-220237 | 8/1997 |
| JP | | 11-028217 | 2/1999 |
| JP | | 11-146889 | 6/1999 |
| JP | | 11-249548 | 9/1999 |
| JP | | 2002-262545 | 9/2000 |
| JP | | 2002-264222 | 9/2002 |
| WO | | WO00/59401 | 10/2000 |

OTHER PUBLICATIONS

The German Office Action, and translation thereof, dated Sep. 6, 2006 issued by the German Patent Office for the corresponding German patent application.

* cited by examiner

OCCLUDATOR, FACE BOW, OCCLUSION-CONFIRMING SYSTEM AND TEMPOROMANDIBULAR JOINT-REPRODUCING SYSTEM

TECHNICAL FIELD

The present invention relates to a dental occludator for confirming occlusion, a face bow for the occludator, an occlusion confirming system which can be used for the fabrication of a prosthesis for teeth and treatment of a temporomandibular joint, etc., and a temporomandibular joint reproducing system usable for the occlusion confirming system.

BACKGROUND ART

As described in JP2000-262545A (see FIG. 1), a conventional occludator comprises, e.g., a lower bow-shaped part where a lower jaw tooth mold is mounted, an upper bow-shaped part where an upper jaw tooth mold is mounted, and a joint for connecting the lower bow-shaped part and the upper bow-shaped part, so that an artificial joint movement such as opening/closing of the tooth molds is obtained and a state of occlusion is reproduced. The occludator is used in the treatment of the occlusion of upper and lower teeth and the fabrication of prostheses.

The joint described in the conventional document is configured such that a maxillary rotation axis (2), which is combined with the upper bow-shaped part and is circular in cross section, is placed from above at a sagittal condyle path tilt angle on a concave combined with the lower bow-shaped part. A plate spring (3) applies an urging force to prevent detachment. A target joint movement is intended to be reproduced by specifying the sagittal condyle path tilt angle.

JP11-28217A (see FIG. 4) describes another form of a conventional occludator. The joint of the occludator is constituted of a condyle (12) composed of a sphere which is mounted on a lower bow-shaped part and protrudes upward, and a condyle box (17) mounted on an upper bow-shaped part. An articular fossa (condyle path) is represented by a plane of the condyle box.

According to the occludator of the latter conventional example, a Benette lift mechanism (15) for lifting an upper jaw tooth mold, from the condyle, separately from the condyle box is provided on the lower bow-shaped part (base). Thus, with respect to the position of the lower jaw tooth mold which is faithfully and accurately mounted as in a state of a living body, reset can be arbitrarily made on the occludator to a lower jaw position diagnosed as the most suitable for a living body, so that a target joint movement is obtained.

In the conventional occludator, the theory of overcompensation reproduction is used. The configuration of the joint is devised and the joint is adjusted on the basis of the overcompensation theory. In the theory of overcompensation reproduction, by setting a condyle path regulating mechanism of the occludator to make movements slightly more than the temporomandibular joint movements of an actual living body, prostheses fabricated on the occludator readily make diastases during lateral movements in an oral cavity. With this theory, even on an occludator less capable of adjustment, moderate prostheses can be fabricated with just a few adverse actions.

However, some errors inevitably occur in mandibular movements reproduced by a semi-adjustable occludator which is less capable of adjustment. A prosthesis fabricated by such an occludator may cause an error which is collision with or separation from opposed teeth during lateral movements. Particularly when providing balanced occlusion for a full denture, a prosthesis may fail due to any of these errors.

Diastasis (right and left artificial teeth of a full denture occlude on a working side and separate on a balanced side) does not cause any problems when prostheses are fabricated for a few teeth. However, when a number of teeth are lost or in the case of a full denture, a stretch of the theory suggests that flat surfaces are better for the occlusion planes of artificial teeth, which may lead to misinterpretation. Flat occlusion planes have low mastication efficiency and cause an enormous load on alveoli and periodontia. Thus, flat surfaces are not always preferable. Rather than flat surfaces, the cusps of molars should be sharpened as much as possible.

In this sense, various kinds of average value occludators (an average value is used as a condyle path angle), semi-adjustable occludators, and totally adjustable occludators (although a condyle path angle can be personally adjusted, the adjustment is difficult and is not correct in a three-dimensional manner) are conventionally produced and prostheses have been fabricated by reproducing occlusion by means of the occludators.

Although various kinds of inventions are devised for joint movements on occludators as described in the conventional examples, the inventions are all based on a joint structure composed of a rod or sphere circular in cross section. An angle, a position, etc. are intended to be adjusted in compliant with the overcompensation theory to obtain joint movements required for prostheses but an actual joint shape is not intended to be reproduced. That is, as described above, dental care workers conventionally comply with the theory of overcompensation reproduction and have no idea about reproduction of an actual shape of a temporomandibular joint. This fact is evident from JP11-146889A which relates to an invention of an artificial temporomandibular joint. In this invention, an articular head is shaped like a rugby ball.

In this invention, a face bow is used to obtain an occlusion plane relative to a predetermined standard plane (e.g., a standard plane such as the Frankfurt plane and the Camper's plane) of a target patient and reproduce the plane on an occludator.

In the conventional face bow, for example, ear rods provided on the ends of right and left legs are inserted respectively into the external auditory meatuses of a patient, the body of the face bow is disposed on the predetermined standard plane, and the occlusion plane position of the upper jaw of the patient is obtained by a bite fork mounted on the face bow.

Then, the occlusion of an upper jaw tooth mold and a lower jaw tooth mold is positioned on the obtained occlusion plane, and the upper jaw tooth mold and the lower jaw tooth mold are mounted and reproduced on the corresponding occludator.

For example, in the case of an occludator with the Frankfurt plane, when the face bow is mounted on the patient, it is better to set the face bow on the Frankfurt plane. However, as described above, a joint of the occludator is constituted of a sphere and a platy member and thus the face bow does not have to be correctly positioned on the standard plane. According to the mechanism of the conventional face bow, it is difficult to correctly make setting on the standard plane. Thus, the face bow is not so correctly positioned on the standard plane in ordinary cases.

Moreover, the conventional face bow is made of a material not permitting the passage of X-ray beams, e.g., a metal.

DISCLOSURE OF THE INVENTION

The prevent invention is devised in view of the above-described points and has as its object the provision of an occludator which can reproduce a joint movement closer to an actual temporomandibular joint movement of a patient during occlusion and a face bow used for the occludator. Another object is to provide an occlusion confirming system and a temporomandibular joint reproducing system which can reproduce an ideal joint movement or a joint movement closer to an actual temporomandibular joint of a patient during occlusion.

In order to attain the objects, an invention is an occludator comprising a lower bow-shaped part for mounting a lower jaw tooth mold, an upper bow-shaped part for mounting an upper jaw tooth mold, and right and left joints which connect the lower bow-shaped part and the upper bow-shaped part and enable a movement including an opening/closing movement and a lateral movement, characterized in that the joint comprises an artificial condyle which is detachably mounted on the lower bow-shaped part and protrudes upward and an artificial articular fossa which is detachably mounted on the upper bow-shaped part and is opposed to the artificial condyle from above, the artificial condyle and the artificial articular fossa are both identical in contour to the mandibular condyle or the maxillary fossa of a person whose impression has been obtained during the fabrication of the upper jaw tooth model.

Regarding the configuration, an invention is also characterized in that the occludator comprises an elastic body for applying an urging force in a direction of bringing the lower bow-shaped part and the upper bow-shaped part relatively close to each other.

According to the present invention, the opposed artificial condyle and artificial articular fossa can be kept in contact with each other and a smooth joint movement can be obtained.

The invention is also characterized in that the joint is constituted of an upper joint and a lower joint which are opposed to each other, the upper joint is constituted of an upper mounting member supported by the upper bow-shaped part, a maxillary fossa model, and first mounting means for detachably mounting the pedestal of the maxillary fossa model on the upper mounting member and the lower joint is constituted of a lower mounting member fixed on the lower bow-shaped part, a mandibular condyle model, and second mounting means for detachably mounting the pedestal of the mandibular condyle model on the lower mounting member.

According to the present invention, the maxillary fossa model and the mandibular condyle model can be replaceable.

The invention is also characterized in that the first mounting means is constituted of a male screw part formed on the upper mounting member, a cylindrical member having a female screw formed in an inner surface, the female screw enabling to be screwed to the male screw, and an inner flange which is formed integrally with the cylindrical member, forms a hole permitting the passage of the maxillary fossa model, and can make contact with the periphery of the pedestal of the maxillary fossa model, and the periphery of the pedestal of the maxillary fossa model is sandwiched between the upper mounting member and the inner flange by screwing the female screw to the male screw.

According to the present invention, the maxillary fossa model can be attached and detached with ease.

The invention is also characterized in that the second mounting means is constituted of a male screw part formed on the lower mounting member, a cylindrical member having a female screw formed in an inner surface, the female screw enabling to be screwed to the male screw, and an inner flange which is formed integrally with the cylindrical member, forms a hole permitting the passage of the mandibular condyle model, and can make contact with the periphery of the pedestal of the mandibular condyle model, and the periphery of the pedestal of the mandibular condyle model is sandwiched between the lower mounting member and the inner flange by screwing the female screw to the male screw.

According to the present invention, the mandibular condyle model can be attached and detached with ease.

The invention is further characterized in that the first mounting means comprises a ring-shaped part which is formed on an end of the upper mounting member and has an inner concave part permitting the insertion of the pedestal of the maxillary fossa model, and a fixing screw which laterally penetrates the ring-shaped part while being connected to the ring-shaped part by screwing, and has an end screwed inside the pedestal from a part where the female screw is not formed on the side of the pedestal of the maxillary fossa model.

According to the present invention, the maxillary fossa model can be attached and detached with ease.

The invention is also characterized in that the pedestal in cross section and the concave part of the ring-shaped part are both polygonal, and the pedestal is so shaped as to be engaged with the concave part of the ring-shaped part.

According to the present invention, it is possible to readily position the maxillary fossa model in the lateral direction (X-Y direction) and the circumferential direction.

The invention is further characterized in that the second mounting means comprises a ring-shaped part which is formed on an end of the lower mounting member and has an inner concave part permitting the insertion of the pedestal of the mandibular condyle model, and a fixing screw which laterally penetrates the ring-shaped part while being connected to the ring-shaped part by screwing, and has an end screwed inside the pedestal from a part where the female screw is not formed on a side of the mandibular condyle model.

According to the present invention, the mandibular condyle model can be attached and detached with ease.

Also the invention is characterized in that the pedestal in cross section and the concave part of the ring-shaped part are both polygonal, and the pedestal is so shaped as to be engaged with the concave part of the ring-shaped part.

According to the present invention, it is possible to readily position the mandibular condyle model in the lateral direction (X-Y direction) and the circumferential direction.

In addition, the invention is characterized by further comprising upper positioning means for regulating the position of the pedestal of the maxillary fossa model relative to the upper mounting part.

According to the present invention, it is possible to readily adjust a direction when mounting the maxillary fossa model on the upper bow-shaped part.

The invention is also characterized by further comprising lower positioning means for regulating the position of the pedestal of the mandibular condyle model relative to the lower mounting part.

According to the present invention, it is possible to readily adjust a direction when mounting the mandibular condyle model on the lower bow-shaped part.

The invention is further characterized by further comprising position adjusting means for laterally adjusting the position of at least one of the artificial condyle and the artificial articular fossa.

According to the present invention, since a position can be adjusted in the lateral direction, the positions of the right and left joints of the occludator can be adjusted according to a distance between the right and left temporomandibular joints of a target person.

The invention is also characterized in that two or more pairs of the mandibular condyle model and the maxillary fossa model are provided, and a pair of the mandibular condyle model and the maxillary fossa model is used as the artificial condyle and the artificial articular fossa according to the shape of the temporomandibular joint of a person whose impression has been obtain during the fabrication of the upper jaw tooth model.

According to the present invention, it is not necessary to prepare a mandibular condyle model and a maxillary fossa model for each target patient. If the tendency of temporomandibular joints is identified for each target patient, a mandibular condyle model and a maxillary fossa model to be used can be selected from ordinary two-dimensional radiographs.

The invention is further characterized by further comprising connecting parts on a pair of lateral positions in the occludator, the connecting parts connecting the face bow.

The invention is also a face bow which is used for the occludator and reproduces the positional relationship between a temporomandibular joint and an occlusion plane on the occludator, characterized in that the face bow comprises a face bow body having a pair of right and left legs stretching symmetrically, a connecting part which is provided on an end of each leg and can be connected to the connecting part of the occludator, and a nose piece which is supported by the face bow body and brought into contact with a hollow in the upper part of the nose of a patient, the nose piece comprises a position adjusting mechanism capable of adjusting a position at least in the vertical direction and the longitudinal direction with respect to the face bow body, the connecting part provided on the end of the leg is an ear rod which can be inserted into an external auditory meatus of a patient, the connecting part of the occludator is constituted of an insertion hole permitting insertion of the ear rod, the face bow body is made of a material permitting passage of an X-ray beam, and the face bow body comprises a marking member which is laterally opposed to a center of a mandibular condyle of a patient or a vicinity of the center in front of the ear rod and is made of a material not permitting the passage of an X-ray beam, and a supporting member causing the leg to support the marking member.

According to the present invention, when the face bow is adjusted on a standard plane such as the FH plane, the face bow is supported on the head of a patient via at least three points of the ends of the right and left legs and the nose piece. At this point, the nose piece can be adjusted at least in the vertical direction and the longitudinal direction. Thus, by adjusting the position of the nose piece with respect to the face bow body, the face bow can be adjusted on the standard plane while being supported positively on the head of the patient via at least three points.

The invention is also characterized in that the face bow body comprises a level.

According to the present invention, a state of inclination can be readily confirmed by the level. That is, the face bow can be positively leveled and used at the setting of the face bow. In other words, the position of occlusion in a living body can be reproduced on the occludator with higher accuracy.

The invention is further characterized in that the face bow comprises a face bow body having a pair of right and left legs stretching symmetrically, an ear rod which is provided on an end of the leg and can be inserted into an external auditory meatus of a patient, and a nose piece which is supported by the face bow body and brought into contact with a hollow on an upper part of a nose of a patient, the face bow further comprises a regulating mechanism for sliding the pair of right and left legs only in a lateral direction.

The invention is also characterized in that the face bow body is made of a material permitting the passage of an X-ray beam, and the face bow body comprises a marking member which is laterally opposed to the center of a mandibular condyle of a patient or the vicinity of the center in front of the ear rod and is made of a material not permitting the passage of an X-ray beam, and a supporting member causing the leg to support the marking member Further, the present invention provides an occlusion confirming system characterized in that the system comprises a CT device for photographing a temporomandibular joint of a target person, a stereolithography machine for forming a solid model of the temporomandibular joint on the basis of three-dimensional image data of the temporomandibular joint specified by image information photographed by the CT device, and an occludator including a lower bow-shaped part for mounting a lower jaw tooth mold, an upper bow-shaped part for mounting an upper jaw tooth mold, and right and left joints for connecting the lower bow-shaped part and the upper bow-shaped part, the joint comprises an artificial condyle which is mounted on the lower bow-shaped part and protrudes upward and an artificial articular fossa which is mounted on the upper bow-shaped part and is opposed to the artificial condyle from above, the artificial condyle and the artificial fossa are each constituted of the solid model formed by the stereolithography machine, and the solid models of the artificial condyle and the artificial articular fossa are integrally formed in a separable manner.

The invention is also characterized by further comprising an elastic body for applying an urging force in a direction of bringing the lower bow-shaped part and the upper bow-shaped part relatively close to each other.

According to the present invention, the opposed artificial condyle and artificial articular fossa can be kept in contact with each other and a smooth joint movement can be obtained.

The invention is also characterized in that the joint is constituted of an upper joint and a lower joint which are opposed to each other, the upper joint is constituted of an upper mounting member supported by the upper bow-shaped part, a maxillary fossa model, and first mounting means for detachably mounting the pedestal of the maxillary fossa model on the upper mounting member, and the lower joint is constituted of a lower mounting member fixed on the lower bow-shaped part, a mandibular condyle model, and a second mounting means for detachably mounting the pedestal of the mandibular condyle model on the lower mounting member.

According to the present invention, the maxillary fossa model and the mandibular condyle model can be replaceable.

The invention is also characterized in that the first mounting means is constituted of a male screw part formed on the upper mounting member, a cylindrical member having a female screw formed in an inner surface, the female screw enabling to be screwed to the male screw, and an inner flange which is formed integrally with the cylindrical member, forms a hole permitting the passage of the maxillary fossa model, and can make contact with the periphery of the pedestal of the maxillary fossa model, and the periphery of the pedestal of the maxillary fossa model is sandwiched between the upper mounting member and the inner flange by screwing the female screw to the male screw.

According to the present invention, the maxillary fossa model can be attached and detached with ease.

The invention is also characterized in that the second mounting means is constituted of a male screw part formed on the lower mounting member, a cylindrical member having a female screw formed in an inner surface, the female screw enabling to be screwed to the male screw, and an inner flange which is formed integrally with the cylindrical member, forms a hole permitting the passage of the mandibular condyle model, and can make contact with the periphery of the pedestal of the mandibular condyle model, and the periphery of the pedestal of the mandibular condyle model is sandwiched between the lower mounting member and the inner flange by screwing the female screw to the male screw.

According to the present invention, the mandibular condyle model can be attached and detached with ease.

The invention is further characterized in that the first mounting means comprises a ring-shaped part which is formed on an end of the upper mounting member and has an inner concave part permitting the insertion of the pedestal of the maxillary fossa model, and a fixing screw which can laterally penetrate the ring-shaped part while being connected to the ring-shaped part by screwing, and has an end capable of being screwed inward or in contact with the side of the pedestal of the maxillary fossa model.

According to the present invention, the maxillary fossa model can be attached and detached with ease.

The invention is also characterized in that the second mounting means comprises a ring-shaped part which is formed on an end of the lower mounting member and has an inner concave part permitting the insertion of the pedestal of the mandibular condyle model, and a fixing screw which can laterally penetrate the ring-shaped part while being connected to the ring-shaped part by screwing, and has an end capable of being screwed inward or in contact with the side of the pedestal of the mandibular condyle model.

According to the present invention, the mandibular condyle model can be attached and detached with ease.

The invention is also characterized by further comprising upper positioning means for regulating the position of the pedestal of the maxillary fossa model relative to the upper mounting part.

According to the present invention, it is possible to readily adjust a direction when mounting the maxillary fossa model on the upper bow-shaped part.

The invention is also characterized by further comprising lower positioning means for regulating the position of the pedestal of the mandibular condyle model relative to the lower mounting part.

According to the present invention, it is possible to readily adjust a direction when mounting the mandibular condyle model on the lower bow-shaped part.

The invention is also characterized by further comprising position adjusting means for laterally adjusting the position of at least one of the artificial condyle and the artificial articular fossa.

According to the present invention, since a position can be adjusted in the lateral direction, the positions of the right and left joints of the occludator can be adjusted according to a distance between the right and left temporomandibular joints of a target person.

In addition, the invention is characterized by further comprising a face bow including a face bow body which is used for reproducing the positional relationship between the temporomandibular joint and an occlusion plane on the occludator and has a pair of right and left legs stretching symmetrically, characterized in that at least the right and left legs are made of a material permitting the passage of a light beam used in the CT device, and at least one marking member is provided on an end of each of the right and left legs, the marking member being made of a material not permitting the passage of the light beam.

The present invention is preferable when a local irradiation CT device is used, which does not photograph right and left temporomandibular joints at the same time in consideration of a radiation dose and so on.

According to the present invention, the marking member is also photographed close to an image of a temporomandibular joint during the photographing of the CT device. Thus, it is possible to calculate a distance between a temporomandibular joint hidden in a living body and the adjacent marking member, that is, a distance between an end of the face bow and an adjacent temporomandibular joint from the image data.

Further, a distance between right and left temporomandibular joints can be determined by determining a distance between the right and left ends of the face bow, so that the right and left joints on the occludator can be set according to a distance between actual temporomandibular joints.

The invention is characterized in that the face bow comprises a nose piece which is supported by the face bow body and brought into contact with a hollow in the upper part of the nose of a patient, and the nose piece comprises a position adjusting mechanism capable of adjusting a position at least in the vertical direction and the longitudinal direction with respect to the face bow body.

According to the present invention, by adjusting the position of the nose piece with respect to the face bow body, the setting position of the face bow body can be readily adjusted on a standard plane such as the FH plane.

The invention is further characterized in that the face bow body comprises a level.

According to the present invention, a degree of levelness of the face bow body can be visually recognized with ease by the level. That is, the position of occlusion in a living body can be reproduced on the occludator with higher accuracy.

The invention is characterized in that the marking member is disposed on a position presumed to be laterally opposed to the center of the mandibular condyle of a patient.

The invention is also characterized by further comprising an ear rod on an end of the leg in the face bow, the ear rod being inserted into an external auditory meatus of a patient, and each of the right and left sides of the occludator has an insertion hole for the insertion of the ear rod.

The invention also comprises a headgear fixed on the head of a target person, characterized in that the head gear comprises right and left connecting parts for temporarily connecting the right and left ends of the face bow and connection position adjusting means for adjusting the position of the connecting part to a predetermined position.

According to the present invention, the right and left ends of the face bow can be set to desired positions. The position of the connecting part is preferably set on lateral position of the center of a target mandibular condyle (lateral position on the same horizontal plane as the center of the mandibular condyle).

The position of the connecting part is varied according to the size of a head, etc., and can be adjusted by the connection position adjusting means.

The invention is characterized in that the headgear comprises fixing means for temporarily fixing the headgear to the CT device.

According to the present invention, the headgear is temporarily fixed on the CT device, so that the head is fixed during the photographing of the CT device and the setting position is not varied.

The invention 38 is an occlusion confirming system, characterized in that the system comprises a CT device for photographing a temporomandibular joint of a target person, a stereolithography machine for forming a solid model of the temporomandibular joint on a basis of three-dimensional image data of the temporomandibular joint specified by image information photographed by the CT device, and an occludator including a lower bow-shaped part for mounting a lower jaw tooth mold, an upper bow-shaped part for mounting an upper jaw tooth mold, and right and left joints for connecting the lower bow-shaped part and the upper bow-shaped part, the joint comprises an artificial condyle which is mounted on the lower bow-shaped part and protrudes upward and an artificial articular fossa which is mounted on the upper bow-shaped part and is opposed to the artificial condyle from above, and at least one of the artificial condyle and the artificial articular fossa is constituted of the solid model formed by the stereolithography machine, and a database for storing ideal model information about a temporomandibular joint condyle, is characterized by further comprising data correcting means for correcting three-dimensional data on the temporomandibular joint condyle specified by image information photographed by the CT device such that the contour of the temporomandibular joint condyle specified by the image information photographed by the CT device is identical to a contour protruding closer to an ideal model, when a comparison is made between the contour of the temporomandibular joint condyle specified by the image information photographed by the CT device and the corresponding ideal model on the database and it is decided that the temporomandibular joint condyle wears more than a predetermined degree.

According to the present invention, when the top of an actual mandibular condyle wears more than a predetermined degree, a correction is made to a protrusion of a mandibular condyle presumed to be close to a healthy condition, occlusion close to the healthy condition is reproduced on the occludator, and prostheses are constructed according to the occlusion. Thus, it is possible to obtain occlusion close to the healthy state in a living body and the temporomandibular joint may be restored to a normal condition.

Further, three-dimensional data may be stored at a younger age and a protrusion may be corrected according to the stored data.

The invention also provides a temporomandibular joint reproducing system characterized by comprising a CT device for photographing a temporomandibular joint of a target person, and a stereolithography machine for forming a solid model of a temporomandibular joint on the basis of three-dimensional data of the temporomandibular joint specified by image information photographed by the CT device, characterized by further comprising a face bow including a face bow body which is used for reproducing the positional relationship between the temporomandibular joint and an occlusion plane on the occludator and has a pair of right and left legs stretching symmetrically, characterized in that at least the right and left legs are made of a material permitting the passage of a light beam used in the CT device, a marking member is provided on an end of each of the right and left legs on a position presumed to be laterally opposed to the center of the mandibular condyle of a patient, the marking member being made of a material not permitting the passage of the light beam, and a forming area for stereolithography is specified according to the position of the photographed marking member.

A supplementary explanation will be given on the occludator of the present invention and the occludator used for the present invention.

It is expected that the fabrication of the maxillary fossa and the mandibular condyle of a patient and the reproduction of a three-dimensional movement of a mandibular movement would be extremely useful for the fabrication of a large prosthesis as well as a small prosthesis. That is, moderate satisfaction so far is turned to great satisfaction by the present invention and effectiveness is provided for the patient.

Another suggestion will be made below on a condyle path. A condyle path guidance is guided by a maxillary fossa and a mandibular condyle in a manner unique to a patient and cannot be freely changed by an operator. Conventionally this guidance has been regarded as the most important guidance of mandibles. For a person who has lost upper and lower teeth, an occlusion pattern and a cusp angle of teeth (artificial teeth) are determined by the condyle path guidance. When a small condyle path is adjusted for an occludator, in the case of a larger movement, cusps interfere with each other and thus the occludator may not act as means for providing preferred occlusion. Such a problem is avoidable in the adoption of the present invention.

As the conventional occludator, when a joint is constituted of a linear articular fossa and a spherical mandibular condyle and prostheses are fabricated, interference (full denture or a number of lost teeth) may occur in a lateral movement. Such an interference is likely to cause a temporomandibular arthrosis and break teeth. In contrast to the conventional art, the present invention makes it possible to reproduce a temporomandibular joint of each patient in a three-dimensional manner, thereby readily preventing the interference.

Further, the present invention can reproduce an actual temporomandibular joint on the occludator, that is, a state of a temporomandibular joint in a living body can be extracted to the outside. Thus, the present invention is applicable in various fields.

An artificial arm, an artificial leg, or an artificial eye is effective in terms of appearance, whereas original functions cannot be exercised. In this sense, the present invention is advantageous because functions can be reproduced. Therefore, occlusion can be analyzed. Unlike the conventional art, prostheses are fabricated without the need for adjusting various angles. That is, since an actual temporomandibular joint is reproduced, it is expected that the present invention is useful for preventing occlusion interference, premature contact, bruxism, a displacement of a jaw, and an internal deformation of a temporomandibular joint.

A temporomandibular joint is different in form and function from other joints, and thus the characteristic causes of diseases and the progresses of diseases have been hardly clarified due to, for example, difficulty in sampling the materials. Even in the absence of an organic change, it is extremely rare to find completely symmetrical mandibular condyles. Unlike the conventional art, the occludator of the present invention reproduces a size and a form almost equal to actual ones (e.g., an error is 50 μm). Thus, the present invention is useful for the following unexplained diseases: a birth defect on a jaw, growth abnormality, inflammation, an external wound, ankylosis of temporomandibular joint, and a metabolic disease. As described above, the present invention is a ray of hope in clinical diagnosis, treatment, and epidemiography on temporomandibular arthrosis and contributes to treatment and the decision of a cause and progress of a disease.

Moreover, the conventional occludator cannot express a change of an articular fossa and a mandibular condyle between ages. Products have been fabricated only by a linear articular fossa and a contact shaped like a ball. However, the occludator of the present invention can handle a regressive change. A proper load should be applied to an articular fossa and a mandibular condyle all the time. The occludator of the present invention can respond to the need.

BRIEF DESCRIPTION OF THE DRAWINGS

FIG. 22A is a plan view, and FIG. 22B is a side view;

FIG. 24A is a plan view, and FIG. 24B is a side view;

BEST MODE FOR CARRYING OUT THE INVENTION

Embodiment 1 of the present invention will be described below in accordance with the accompanying drawings.

First, the following will discuss the configuration of an occludator K used for the present system.

Figure 1:
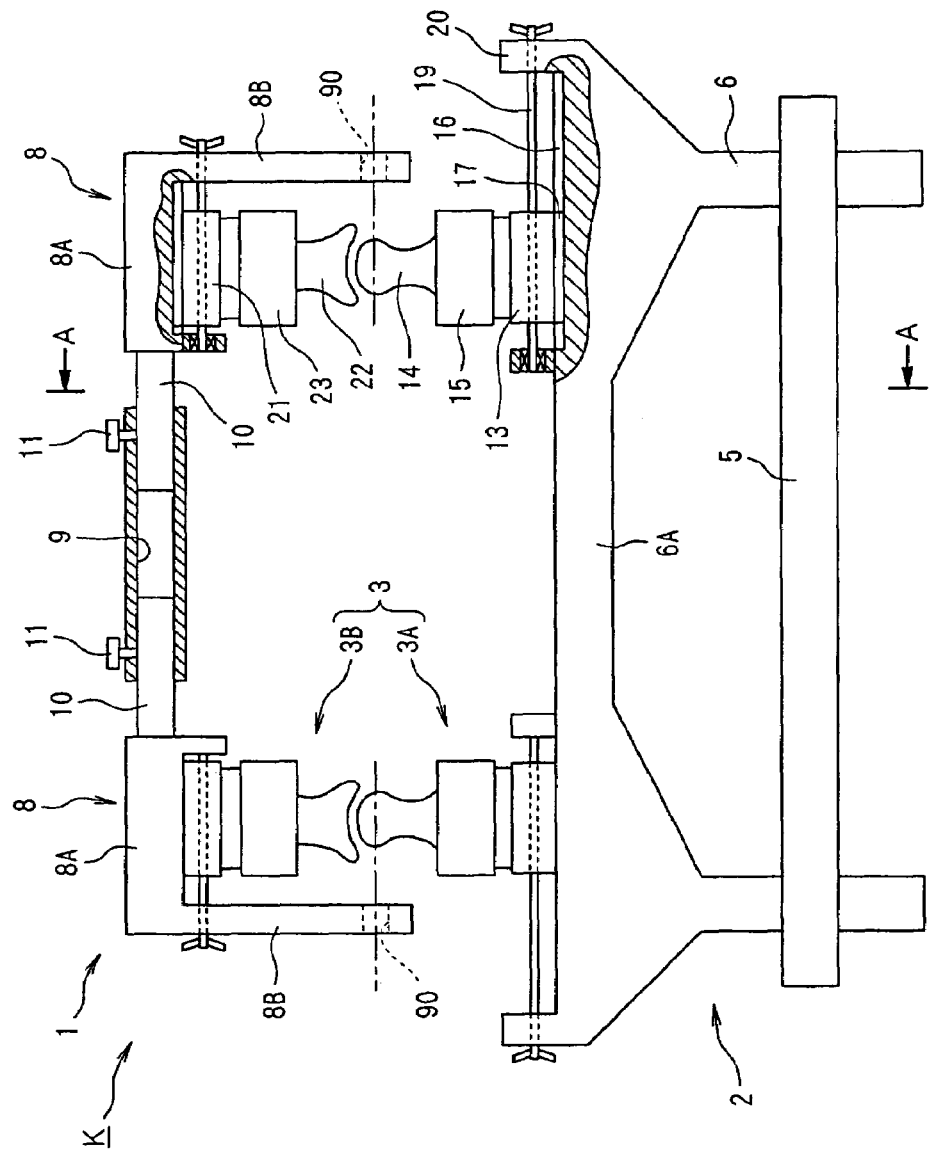
FIG. 1 is a rear view showing an occludator according to Embodiment 1 of the present invention.
Figure 2:
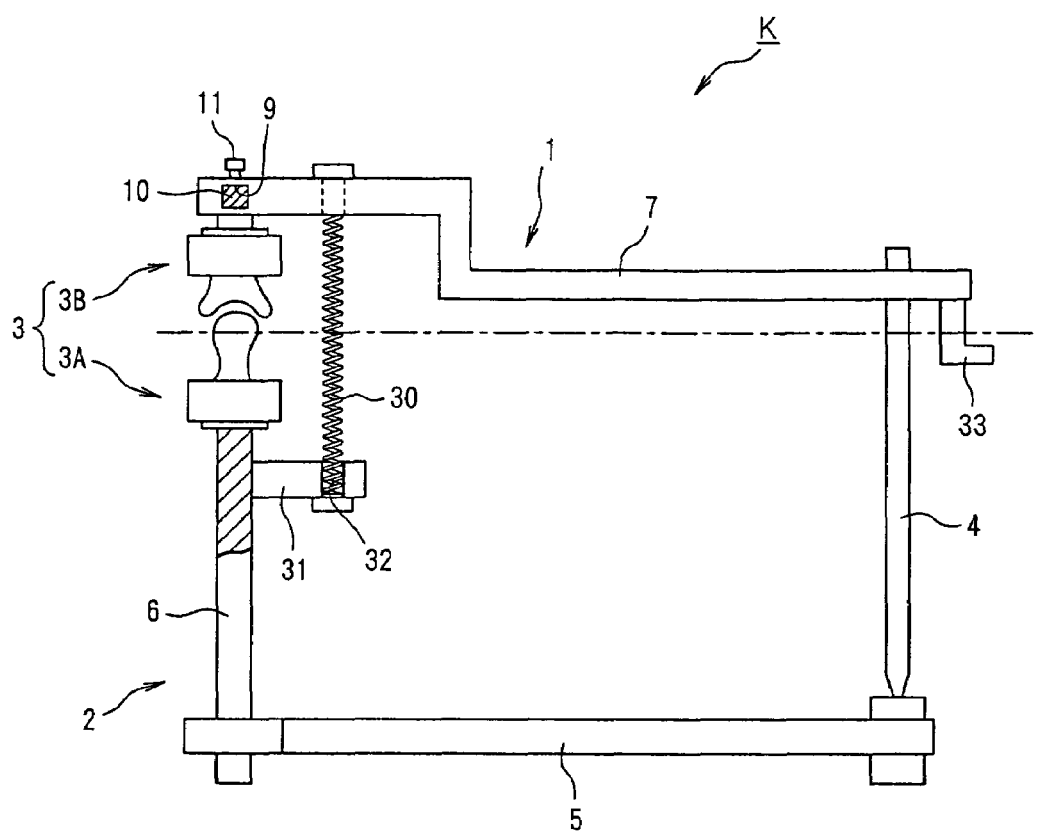
FIG. 2 is a diagram showing an occludator taken along line A-A of FIG. 1 according to Embodiment 1 of the present invention.

As shown in FIGS. 1 and 2, the occludator K of the present embodiment is constituted of an upper bow-shaped part 1, a lower bow-shaped part 2, a joint 3 for connecting the upper bow-shaped part 1 and the lower bow-shaped part 2, and an incisal pin 4. To enhance understanding, a mandibular condyle model 14 and a maxillary fossa model 22, which are vertically opposed to each other, are not in contact with each other in some drawings below. In reality, the models are in contact with each other (contact state) or an elastic sheet material (not shown, the material is made of a material such as silicon and is preferably equal in elastic modulus to an articular disk) equal in thickness to a gap between joints is interposed between the models. Further, to enhance understanding, some parts are omitted in the drawings when necessary as long as no ambiguity occurs.

The lower bow-shaped part 2 is constituted of a lower bow-shaped part body 5 for mounting a lower jaw tooth mold (not shown) and a gate part 6 which rises upward from the rear of the lower bow-shaped part body 5.

The upper bow-shaped part 1 is constituted of an upper bow-shaped part body 7 for mounting an upper jaw tooth mold (not shown) and joint mounting parts 8 which are connected on the right and left to the rear of the upper bow-shaped part body 7. The connecting configuration of the upper bow-shaped part body 7 and the joint mounting parts 8 will be discussed below. A connection is made as follows: an insertion hole 9, which laterally penetrates and is rectangular in cross section, is formed in the rear of the upper bow-shaped part body 7, and bars 10, which protrude respectively from the joint mounting parts 8 and are rectangular in cross section, are inserted into the insertion hole 9. Then, fixing screws 11 are screwed into tapped holes which vertically penetrate in the rear of the upper bow-shaped part body 7 and the ends of the fixing screws 11 are brought into contact with the sides of the bars 10, so that the joint mounting parts 8 on the right and left are fixed to the upper bow-shaped part 1. Further, an amount of insertion of the right and left bars 10 into the insertion hole 9 is adjusted, so that a distance can be adjusted between the right and left joint mounting parts 8. In this case, the bars 10 and the insertion hole 9 are shaped like rectangles. This is because the upper bow-shaped part body 7 can be positively held in a horizontal direction with respect to the joint mounting parts 8.

As shown in FIG. 1, the joint mounting parts 8 on the right and left are each shaped like a letter L in front view (as a matter of course, a box or the like with an open bottom is also applicable). The joint mounting part 8 is constituted of a horizontal part 8A which stretches horizontally along the axis of the bar 10 and a vertical part 8B which vertically stretches downward from the outer end of the horizontal part 8A.

Further, as shown in FIG. 1, the joints 3 on the right and left are provided between the gate part 6 and the right and left joint mounting parts 8. The gate part 6 and the joint mounting parts 8 are vertically opposed to each other.

The joint 3 is configured such that a lower joint 3A mounted on the gate part 6 and an upper joint 3B mounted on the joint mounting part 8 are vertically opposed to each other.

Figure 3:
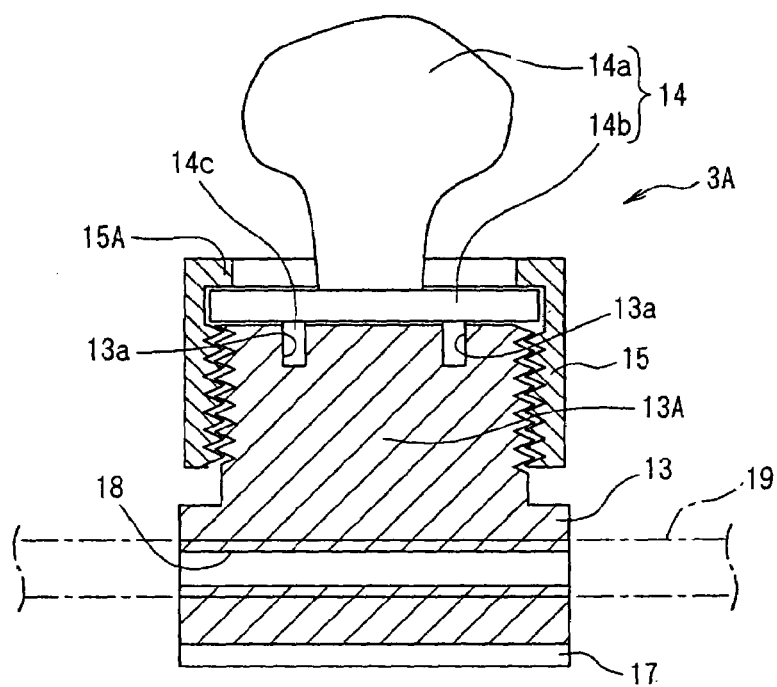
FIG. 3 is a partial sectional view showing the mounting structure of a mandibular condyle model according to Embodiment 1 of the present invention.

As shown in FIGS. 1 and 3, the lower joint 3A is constituted of a lower mounting member 13, the mandibular condyle model 14, and a mounting nut 15 constituting a cylindrical member. The lower mounting member 13 is constituted of a cylindrical member and is supported by a horizontal part 6A of the gate part 6 so as to move only laterally along the upper surface of the horizontal part 6A. The mechanism movable only in the lateral direction is configured by providing, e.g., a guide groove 16 which laterally stretches on the lower surface of the gate part 6 and a guide 17 which is fit into and guided by the guide groove 16 on the lower surface of the lower mounting member 13.

Moreover, the lower mounting member 13 has a female tapped hole 18 laterally penetrating in parallel with the horizontal part 6A. The shaft of a screw 19 is screwed into the female tapped hole 18. The screw 19 is rotationally supported with a bearing or the like by a rising part 20 provided on the horizontal part 6A. Forward/reverse rotations of the screw 19 can adjust the position of the lower mounting member 13 in the lateral direction. The end of the shaft of the screw 19 is also rotationally supported by the horizontal part 6A.

As shown in FIG. 3, the end of the lower mounting member 13 serves as a cylindrical part 13A having a vertical axis. A male screw is cut on the periphery (outer periphery) of the cylindrical part 13A to form a male screw part. Further, the end face of the lower mounting member 13 has two positioning holes 13a.

The mandibular condyle model 14 is constituted of a model body 14a and a disk-like pedestal 14b which is connected to the base of the model body 14a. Two pins 14c protrude downward from the lower end face of the pedestal 14b so as to be inserted into the positioning holes 13a. As will be described later, the mandibular condyle model 14 is formed by stereolithography. In this case, the positioning holes 13a and the pins 14c constitute lower positioning means.

Further, the mounting nut 15 is a member shaped like a cylindrical cap. A female screw screwed to the male screw is formed on the inner surface of the mounting nut 15 and an inward flange 15A is provided on the upper opening of the mounting nut 15. The opening formed by the inward flange 15A is large enough to freely insert the model body 14a. The opening is set smaller in diameter than the pedestal 14b, so that the lower surface of the inward flange 15A can be vertically opposed to the upper surface of the outer periphery of the pedestal 14b.

Then, as shown in FIG. 3, in a state in which the pedestal 14b is brought into contact with the end face of the lower mounting member 13 while positioning is performed by the positioning holes and the pins 14c, the mounting nut 15 is put from above and is screwed and fastened to the cylindrical part 13A of the lower mounting member 13, so that the outer periphery of the pedestal 14b is vertically sandwiched between the end face of the upper mounting member and the lower surface of the inward flange 15A. Thus, the mandibular condyle model 14 is mounted on the horizontal part 8A of the gate part 6.

The upper joint 3 is identical in configuration to the lower joint 3 and is constituted of an upper mounting member 21, the maxillary fossa model 22, and a mounting nut 23 constituting a cylindrical member. The upper mounting member 21 is supported by the horizontal part 8A so as to move only in the lateral direction along the lower surface of the horizontal part 8A of the joint mounting part 8. Further, a screw rotationally supported by the vertical part 8B is screwed into the upper mounting member 21. Forward/reverse rotations of the screw can adjust the position of the upper mounting member 21 in the lateral direction.

The end of the upper mounting member 21 forms a cylindrical part having a vertical axis. A male screw is cut on the periphery of the cylindrical part to form a male screw part. Further, the end face of the lower mounting member has two positioning holes.

The maxillary fossa model 22 is constituted of a model body and a disk-like pedestal which is connected to the base of the model body. Pins protrude upward from the pedestal so as to be inserted into the positioning holes. As will be described later, the maxillary fossa model 22 is formed by stereolithography. In this case, the positioning holes and the pins constitute upper positioning means.

The mounting nut 23 is a member shaped like a cylindrical cap. A female screw screwed to the male screw is formed on the inner surface of the mounting nut 23 and an inward flange is provided on the lower opening of the mounting nut 23. The opening formed by the inward flange is large enough to freely insert the model body. The opening is set smaller in diameter than the pedestal, so that the upper surface of the inward flange can be opposed to the outer periphery of the pedestal. Then, in a state in which the pedestal is brought into contact with the end face of the upper mounting member 21, the mounting nut 23 is put from below and is screwed and fastened to the end of the upper mounting part, so that the outer periphery of the pedestal is vertically sandwiched between the end face of the upper mounting part and the inward flange. Thus, the maxillary fossa model 22 is mounted on the horizontal part 8A.

In this case, on the part of the insertion hole 9 and the right and left bars 10 and the part of the female tapped hole 18 and the screw 19, the lateral position adjusting part constitutes position adjusting means. The two stages illustrate the reproduction of a distance between marking members (described later) and the reproduction of a distance of closest approach (described later).

Figure 4:
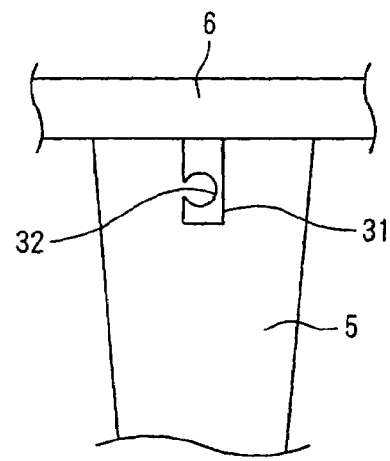
FIG. 4 is a top view showing the lower mounting part of a coil spring according to Embodiment 1 of the present invention.

A coil spring 30, which constitutes an elastic body and has a vertical axis, is disposed at the front of the right and left joints 3 and at the center in the lateral direction. The coil spring 30 has an upper end fixed to the upper bow-shaped part 1 and a lower end detachably mounted on a protrusion 31 protruding from the gate part 6. As shown in FIG. 4, a spring mounting part 32 is notched on a side of the protrusion 31. The spring 30 is inserted from the side, so that the spring 30 can be detachably mounted.

In this case, the number of the springs 30 is not limited to one at the center. Two springs may be disposed symmetrically. Springs may be provided on three or more points. The spring force of the spring can preferably reproduce the elasticity and so on of muscle in some positions.

As shown in FIG. 2, the incisal pin 4 protrudes downward from the front end of the upper bow-shaped part 1, and the end of the incisal pin 4 is in contact with the front end of the lower bow-shaped part 2. A length of the incisal pin 4 from the upper bow-shaped part 1 can be adjusted.

Thus, the upper bow-shaped part 1 is supported by the lower bow-shaped part 2 on three points of the left and right joints 3 and the incisal pin 4, and the maxillary fossa model 22 can be relatively kept in contact with the mandibular condyle model 14 from above by the coil spring 30.

Reference numeral 33 in FIG. 2 denotes a catching part for catching the center of the face bow F. The occludator K is set so as to arrange the chain line of FIG. 2 along the horizontal direction.

The following will describe the fabrication of a solid model serving as the maxillary fossa model 22 and the mandibular condyle model 14, which are used in the occludator K.

Figure 5:
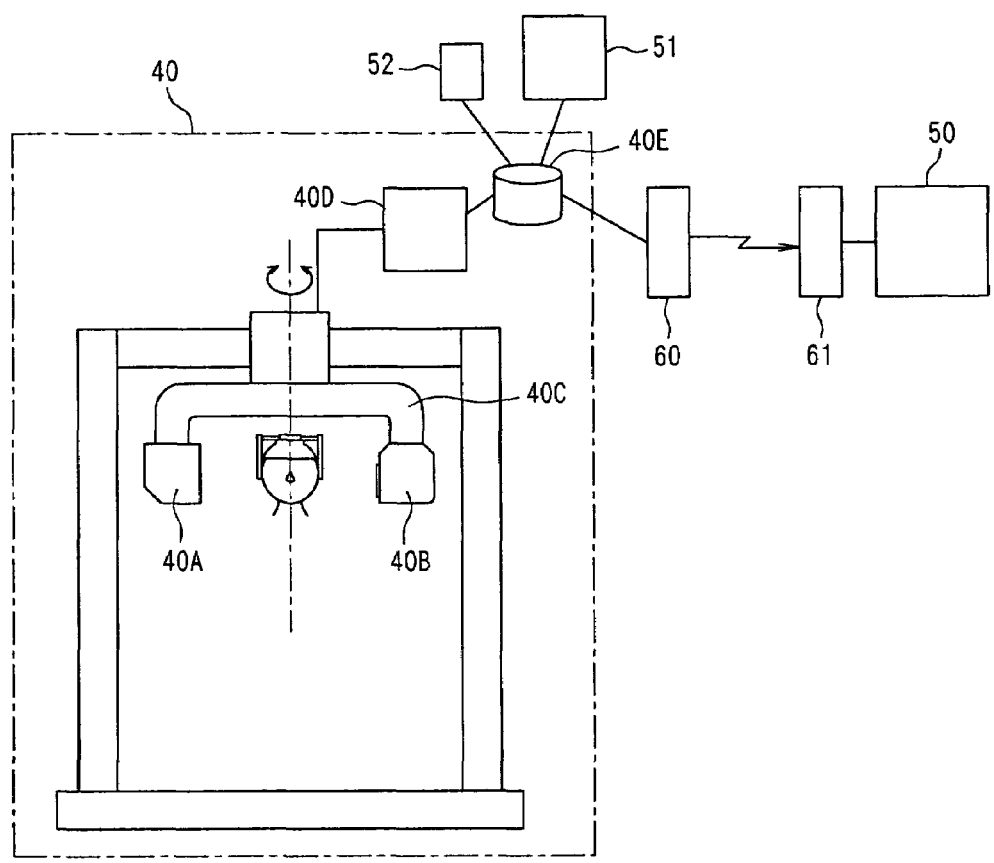
FIG. 5 is a schematic structural diagram showing an occlusion confirming system according to Embodiment 1 of the present invention.

As shown in FIG. 5, the device configuration for fabricating the solid model is constituted of an X-ray CT device 40 and a stereolithography machine 50.

Figure 6:
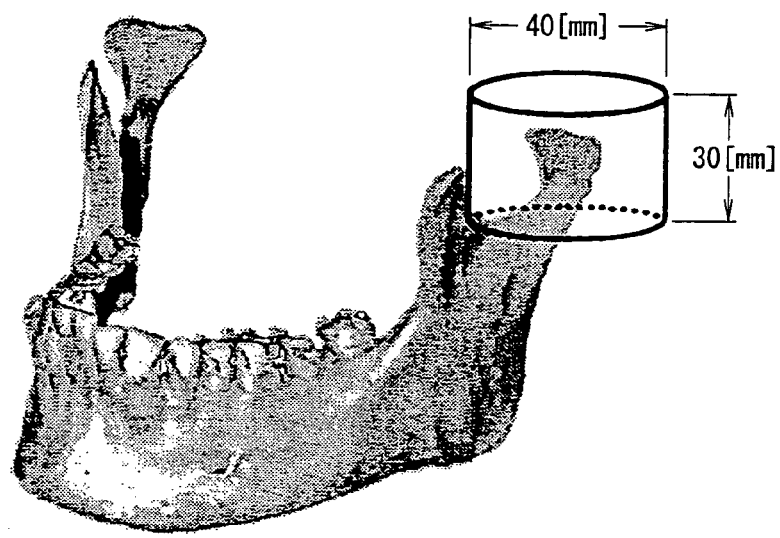
FIG. 6 is a diagram showing a photographing area according to Embodiment 1 of the present invention.

The X-ray CT device 40 photographs a temporomandibular joint area of a target patient that is shown in FIG. 6 and calculates the stereographic data of the temporomandibular joint area from photographic information (image information).

Figure 7:
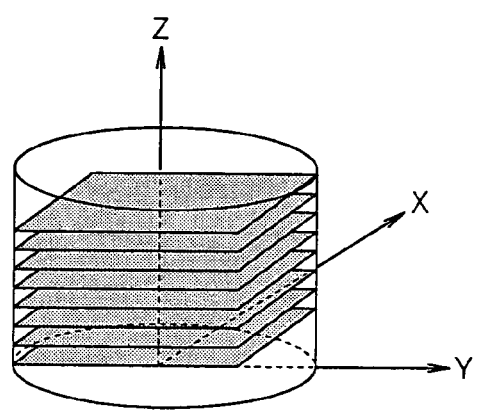
FIG. 7 is a diagram showing an example of a tomogram during stereolithography according to Embodiment 1 of the present invention.

As shown in FIG. 7, from three-dimensional image data calculated and outputted by the X-ray CT device 40, the stereolithography machine 50 cuts out tomograms (binary image) of two or more layers along a predetermined axis (Z axis), determines the contours of the temporomandibular joint from the tomograms, and sequentially overlays the contours while performing photo-curing in the contours, so that a solid model is constructed. Any method is applicable as long as the method belongs to generally known stereolithography.

The solid model may be divided into an articular fossa model and a condyle model after forming the articular fossa model and the condyle model together as the solid model. Alternatively, an articular fossa model and a condyle model may separately undergo stereolithography. The following will describe an example in which the articular fossa model and the condyle model are formed as one solid model.

Regarding the X-ray CT device 40, for example, a local irradiation X-ray CT imaging apparatus disclosed in WO00/57789 is preferable in which a predetermined local area is used as a photographic area. The photographic area is smaller than that of the ordinary medical CT device 40, thereby reducing a dose of radiation to a patient.

The local radiation X-ray CT imaging apparatus at least comprises a rotary arm 40C which opposes an X-ray generator 40A and a two-dimensional X-ray image sensor 40B to each other via the photographic area, position adjusting means which matches the rotating center of the rotary arm 40C and the center of a temporomandibular joint area serving as a subject, rotating means which rotates the rotary arm 40C while locally emitting an X-ray cone beam from the X-ray generator 40A, the X-ray cone beam passing through only the temporomandibular joint area all the time, and calculating means 40D which calculates, by back projection, X-ray projection image information of the temporomandibular joint area obtained by the two-dimensional X-ray image sensor 40B by means of the X-ray cone beam, and calculates three-dimensional projection data (three-dimensional image data) composed of three-dimensional distribution information on an X-ray absorption coefficient of the temporomandibular joint area. In FIG. 5, reference numeral 40E denotes an example of a data storage area.

The local irradiation X-ray CT device 40 successively photographs, as a local photographic area (a cylindrical area shown in FIG. 6), one of the right and left temporomandibular joints 3 of a target patient, calculates three-dimensional image data on the photographic area (temporomandibular joint area) from a plurality of pieces of image information obtained by photographing, and records the three-dimensional image data in the data storage area.

The present embodiment comprises a uniaxial-multidirectional processing section 51 which performs uniaxial-multidirectional processing on three-dimensional image data calculated by the X-ray CT device 40.

Figure 8:
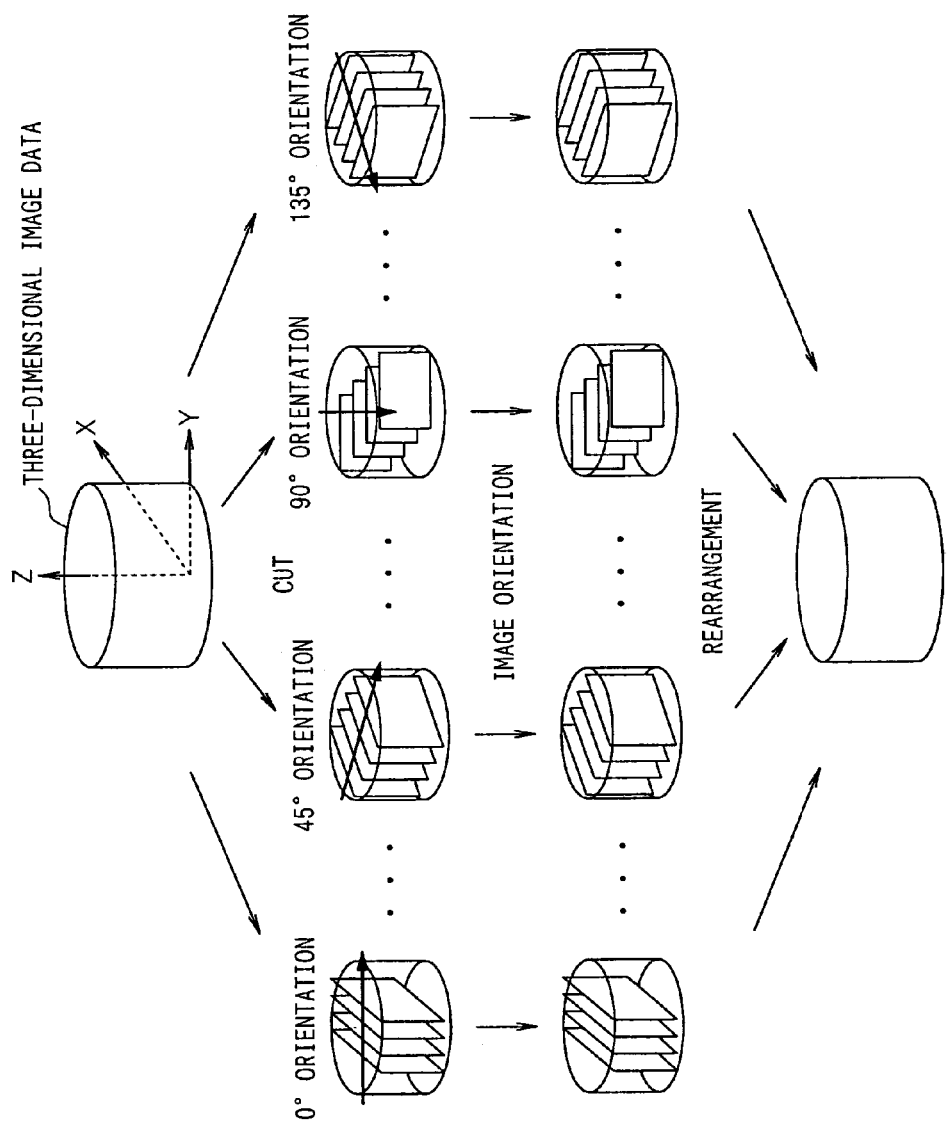
FIG. 8 is a diagram for explaining uniaxial-multidirectional processing according to Embodiment 1 of the present invention.

The uniaxial multidirectional processing section 51 is a noise removing section which lowers a level by temporarily cutting the three-dimensional image data into two-dimensional images along two or more directions, removes noise on the two-dimensional images, and performs rearrangement again in a three-dimensional manner. That is, when three-dimensional image data is cut into two-dimensional images, the uniaxial-multidirectional processing section cuts, e.g., the three-dimensional image data into consecutive two-dimensional images along a plurality of different directions, e.g., along the X-axis direction and the Y-axis direction, and rearranges the consecutive images along the two directions in a three-dimensional manner to reedit the three-dimensional image data. The above explanation described the example where cutting is performed in two directions to lower a level. As shown in FIG. 8, it is preferable to use and rearrange two-dimensional images cut along 16 directions or more orthogonal to the Z axis.

With this uniaxial-multidirectional processing, during stereolithography, surface information lost by cutting into consecutive two-dimensional images along one direction (e.g., Z axis) is interpolated by two-dimensional images cut in other directions and is rearranged into three-dimensional image data with higher accuracy. As a result, also regarding a solid model of a temporomandibular joint that is formed by stereolithography from two-dimensional images having been cut along the Z axis, it is possible to obtain a solid model of a temporomandibular joint with more accurate stereolithography. The noise removing method of the three-dimensional image data is not limited to the uniaxial-multidirectional processing. Moreover, smoothing may be performed during stereolithography.

As described above, when obtaining three-dimensional image data on a target temporomandibular joint from the X-ray CT device 40, the stereolithography machine 50 determines consecutive two-dimensional sectional data (binary tomograms) along the Z axis from the three-dimensional image data, performs photo-curing to obtain the two-dimensional contours of the two-dimensional sectional data, and repeatedly overlays the contours, so that a resin solid model of a temporomandibular joint is fabricated. In this configuration, the disk-like pedestal 14*b* is integrally formed on the connecting portion (base) of the mandibular condyle model 14 and the articular fossa model in each solid model, and the protrusions for positioning are formed on the pedestal 14*b* as described above.

When the mandibular condyle model 14 and the temporomandibular joint fossa model are formed integrally, a gap corresponding to the joint disk is formed between the joints so as to prevent the mandibular condyle model 14 and the temporomandibular joint fossa model from being in contact with each other, and one or more supports (columns, etc.) are interposed between the joints vertically opposed to each other, so that the models are formed while maintaining the gap. For example, two or three columns with a diameter of about 2 to 3 mm can sufficiently act as the supports.

In the device configuration shown in FIG. 5, considering that the installation position of the X-ray CT device 40 and the installation position of the stereolithography machine 50 are separated from each other, the example is illustrated where three-dimensional image data calculated by the X-ray CT device 40 or consecutive two-dimensional image data along the Z axis is transmitted via communication means such as the Internet. Reference numerals 60 and 61 illustrate a transmitter and a receiver.

In this case, photographing and stereolithography of the X-ray CT device 40 are separately performed on the right and left temporomandibular joints 3.

Then, as shown in FIG. 1, the mandibular condyle model 14 and the maxillary fossa model 22, which are formed by stereolithography, are mounted on the joints 3 of the occludator K.

The solid model is obtained by stereolithography before the separation of the mandibular condyle model 14 and the maxillary fossa model 22 which are vertically connected to each other.

That is, in order to match a distance between the centers of the condyles of mandibular condyle models 14 mounted on the right and left of the occludator K with an actual distance between the right and left temporomandibular joint condyles of a patient, an amount of insertion of the right and left bars 10 is adjusted relative to the insertion hole 9, and the positions of the mandibular condyle models 14 and the maxillary fossa models 22 on the right and left are adjusted relative to the horizontal parts 8A by forward/reverse rotations of the screws.

The constructed solid model is mounted in a state in which the mandibular condyle model 14 and the maxillary fossa model 22 are integrally formed. Thus, for example, position adjustment is made such that the pins 14*c* are inserted into the positioning holes 13*a* of the lower mounting member on the side of the gate part 6 of the lower bow-shaped part 2 and are temporarily mounted, the position of the upper mounting member 21 is adjusted, and the pins on the side of the maxillary fossa model 22 of the solid model are inserted into the corresponding positioning holes of the upper mounting member. Thereafter, the mandibular condyle model 14 and the maxillary fossa model 22 are separated from each other and are fixed by the mounting nuts 15 and 23, respectively. In the case of a mechanism where screws are in contact with each other and are fixed (described later), fixing to the mounting members can be completed before the separation of the mandibular condyle model 14 and the maxillary fossa model 22.

The mandibular condyle model 14 and the maxillary fossa model 22 are mounted in the occludator K while being integrated with each other, and then the mandibular condyle model 14 and the maxillary fossa model 22 are separated from each other. The configuration is not limited to the above. The mandibular condyle model 14 and the maxillary fossa model 22 may be separated from each other before being mounted in the occludator K. However, when the models are separated after being mounted in the occludator K, it is possible to faithfully reproduce the positional relationship between the temporomandibular joint condyle and the temporomandibular joint fossa vertically while upper and lower teeth occlude each other.

Besides, the spring 30 having a vertical axis is temporarily removed when the mandibular condyle model 14 and the maxillary fossa model 22 are mounted in the occludator K.

The following will describe a headgear H and the face bow F which are suitable for readily adjusting the right and left positions of the occludator K with high accuracy.

First, the face bow F will be discussed below.

Figure 9:
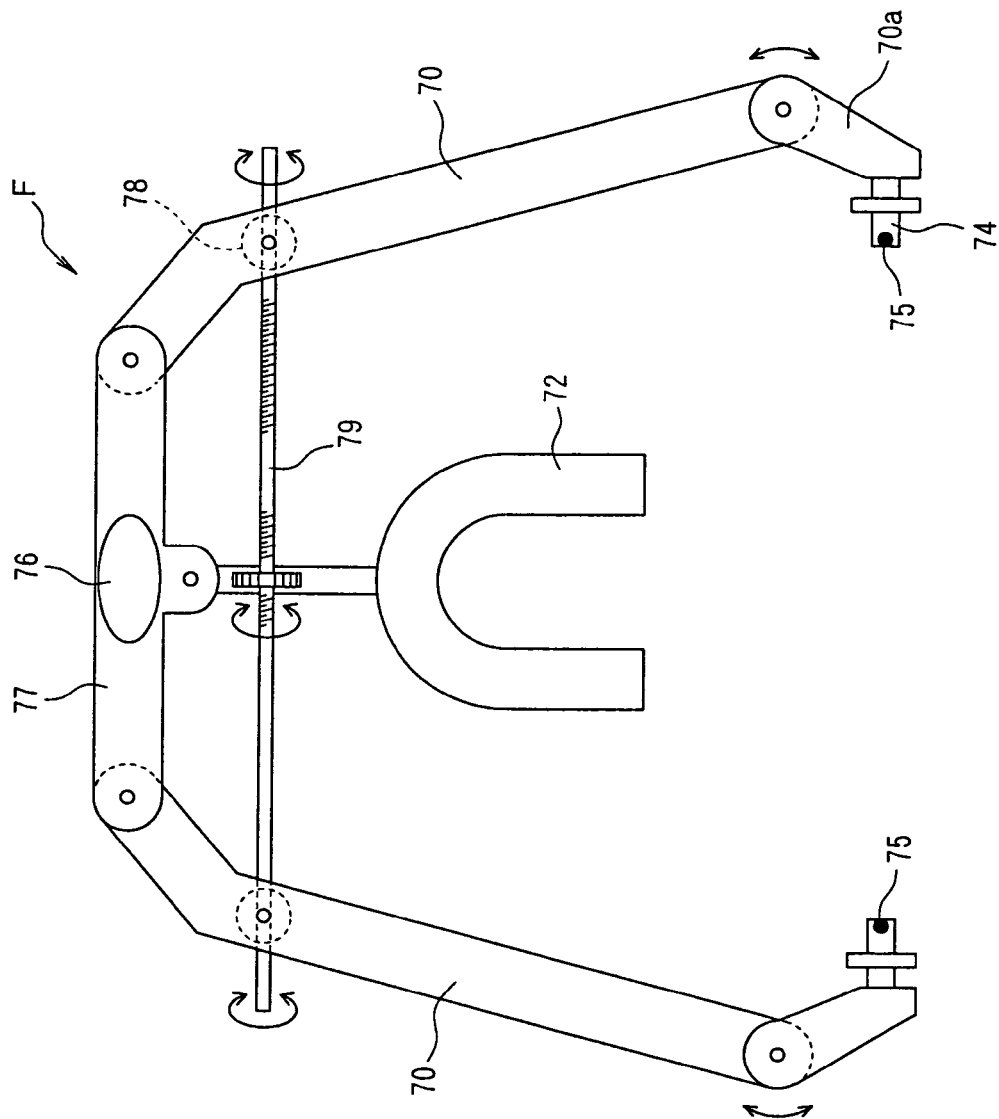
FIG. 9 is a plan view showing a face bow according to Embodiment 1 of the present invention.
Figure 10:
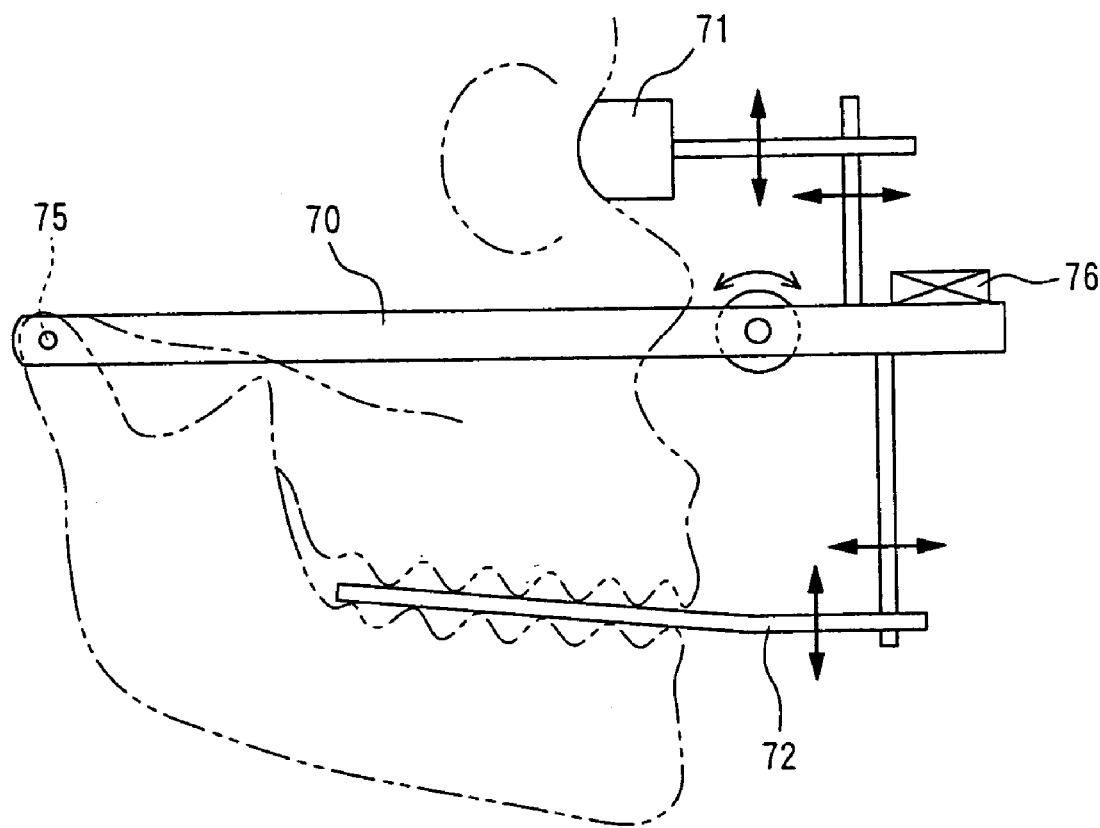
FIG. 10 is a side view showing the face bow according to Embodiment 1 of the present invention.

As shown in FIGS. 9 and 10, the basic configuration is similar to that of the conventional face bow F. Two legs 70 on the right and left are platy members which are opposed to each other so as to rotate almost along a horizontal plane. As with the conventional face bow, the face bow F is provided with a nose piece 71 which is in contact with a hollow in the upper part of the nose of a patient and a bite fork 72 which is bitten by the patient. The positions of the nose piece 71 and the bite fork 72 can be adjusted in the vertical and longitudinal directions with respect to the face bow F.

The face bow F is mainly characterized as follows:

The body of the face bow F is made of a radiolucent material and a material of predetermined strength, e.g., duralumin, an acrylic sheet, a baking plate, fiber reinforced plastics, and so on. A transparent material is more preferable.

A marking member 75 for positioning a condyle is mounted on the end of a stick-like insertion part 74 protruding from the end of each of the right and left legs 70. The marking member 75 is made of a material not permitting the passage of X-ray beams, e.g., a stainless ball and so on.

A level 76 for checking the degree of levelness of the face bow F is mounted.

The configuration of the face bow F shown in FIG. 9 comprises a central plate 77 stretching in the lateral direction and the right and left legs 70 which are connected to the right and left ends of the center plate 77 so as to rotate about vertical axes. Further, on the sides of the central plate, the right and left legs 70 have nut bodies 78 which are mounted so as to rotate about the vertical axes. A threaded rod 79 having an axis in the lateral direction is screwed into the right and left nut bodies 78. A distance between the right and left legs 70 can be adjusted by forward/reverse rotations of the threaded rod 79.

Further, ends 70*a* of the right and left legs 70 can also rotate about the vertical axes, and the marking members 75 are fixed on the ends of protrusions formed on the ends of the legs 70. The protrusions constitute a connecting part on the side of the face bow F.

Moreover, the nose piece 71 and the bite fork 72 are supported by the central plate 77. The front side and back side of the U-shaped part of the bite fork 72 are serrated and thus a material for sampling occlusion can readily stick to the front and back sides.

Figure 11:
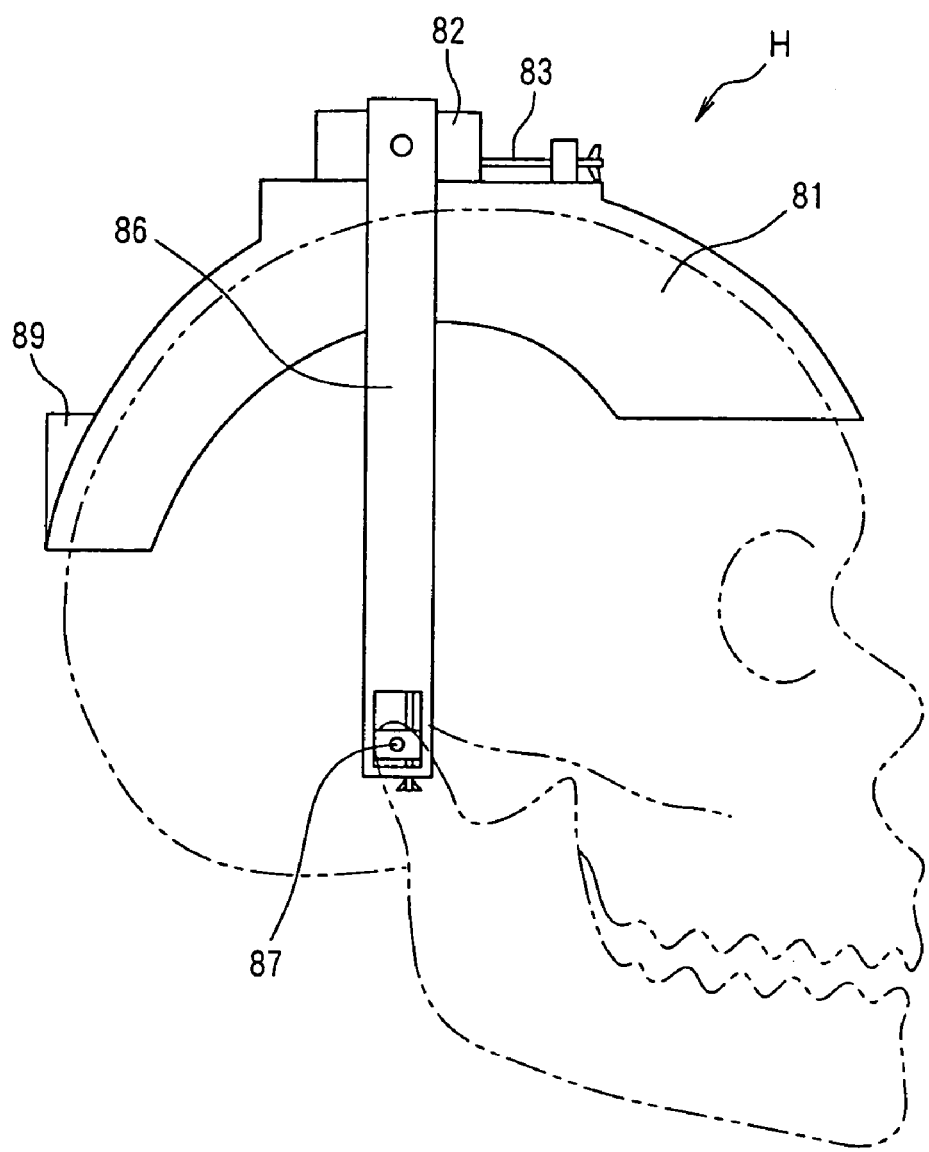
FIG. 11 is a side view showing a headgear according to Embodiment 1 of the present invention.
Figure 12:
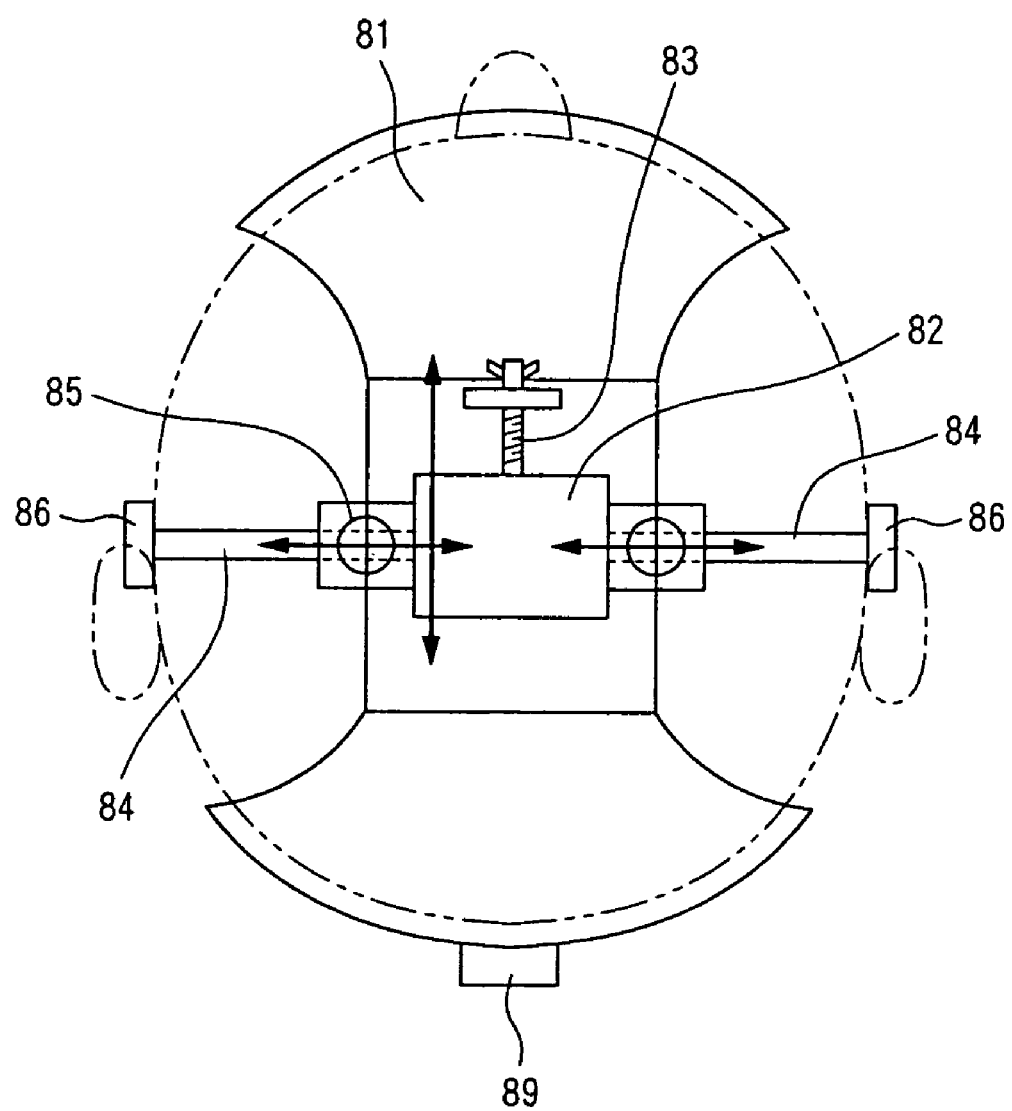
FIG. 12 is a top view showing the headgear according to Embodiment 1 of the present invention.
Figure 13:
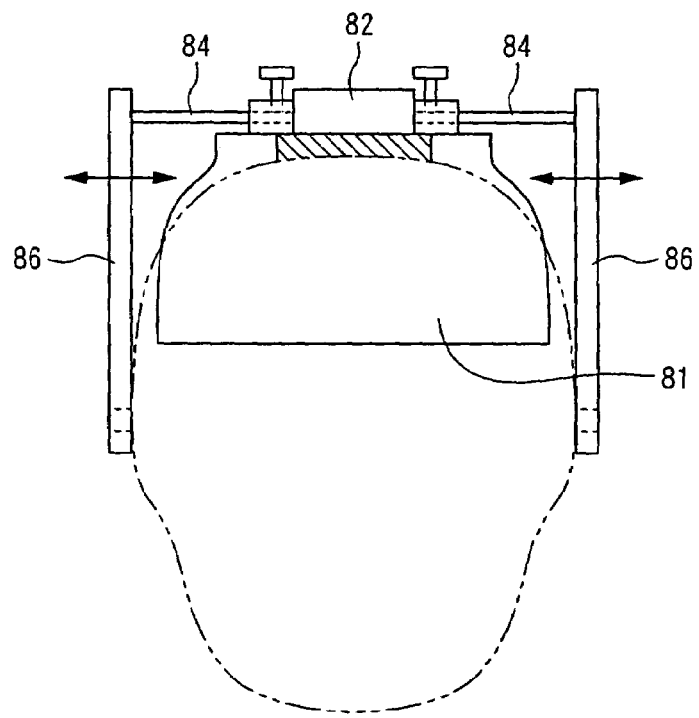
FIG. 13 is a front view showing the headgear according to Embodiment 1 of the present invention.

The headgear H will be discussed below. As shown in FIGS. 11 to 13, the head gear H comprises a headgear body 81 to be mounted on the head of a patient. The top of the headgear body 81 is flattened, a slider 82 is supported so as to move only to the front and back of the top, and a longitudinal adjustment screw 83 rotationally supported on the headgear body 81 is screwed into the slider 82. Moreover, the longitudinal adjustment screw 83 is turned in the forward/reverse direction, so that the slider 82 moves forward and backward to adjust a position in the longitudinal direction.

Further, bars 84 stretch laterally from the slider 82. The bars 84 are inserted into an insertion hole provided in the slider 82 and an amount of lateral protrusion can be adjusted according to an amount of insertion. The end of a screw 85 makes a contact so as to fix the bar 84 with a predetermined length.

Figure 14:
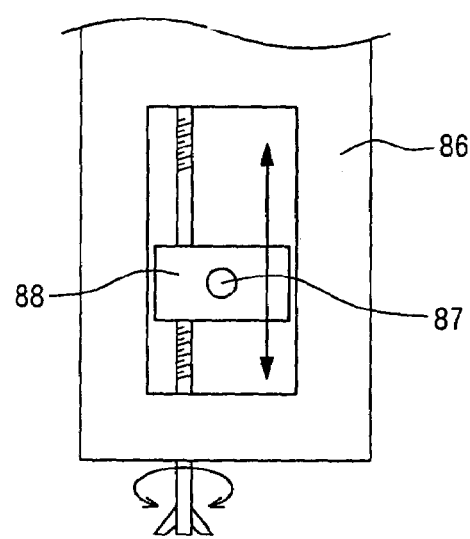
FIG. 14 is a diagram for explaining a vertical position adjusting mechanism according to Embodiment 1 of the present invention.

Moreover, a face bow F mounting body 86 stretching downward is fixed on the end of the bar 84. A face bow F insertion hole 87 constituting a connecting part is provided on the end of the face bow F mounting body 86. As shown in FIG. 14, the position of a portion 88 of the face bow F insertion hole 87 can be vertically adjusted by a screw mechanism.

Further, the rear of the headgear body 81 comprises a fixing part 89 for fixing the headgear H to the frame or the like of the X-ray CT device 40. The fixing part 89 is constituted of a hook mechanism, a screw mechanism, and so on.

The following will discuss the use of the headgear H and the face bow F.

First, when the temporomandibular joint 3 is photographed using the X-ray CT device 40 as shown in FIG. 5, the headgear H is mounted on the head of a patient and the headgear H is fixed on the X-ray CT device 40. The headgear H is fixed on the X-ray CT device 40 in order to prevent the head from swaying during photographing. The head may be restrained with a band as necessary for fixing. Moreover, the headgear itself is not limited to the above configuration. The body of the headgear may be formed by two or more bands.

When the headgear H is mounted, an amount of protrusion of the right and left bars 84 from the slider 82 is adjusted according to the size of the head. The longitudinal position of the slider 82 serving as connecting position adjusting means and the vertical position of the hole are adjusted so as to position the right and left face bow F insertion holes 87 on the sides of the central position of the mandibular condyles of the patient. In general, the side position of the center of the mandibular condyles is disposed about 12 mm forward from the upper edge of a tragus to an angulus oculi lateralis and about 5 mm lower. Thus, the adjustment is made using this position as a guide.

Figure 15:
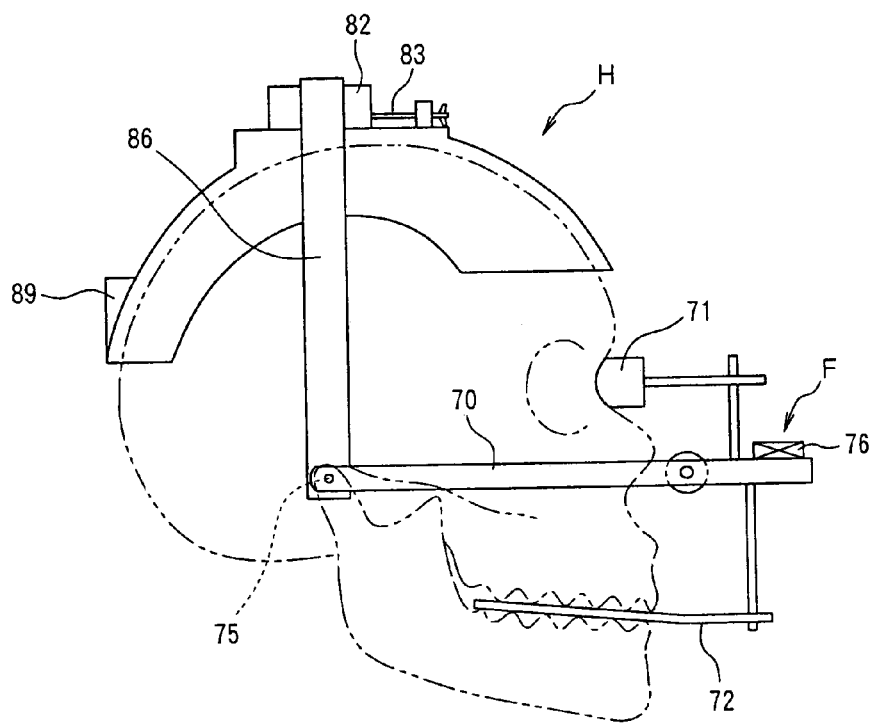
FIG. 15 is a side view showing the relationship between the headgear and the face bow according to Embodiment 1 of the present invention.
Figure 16:
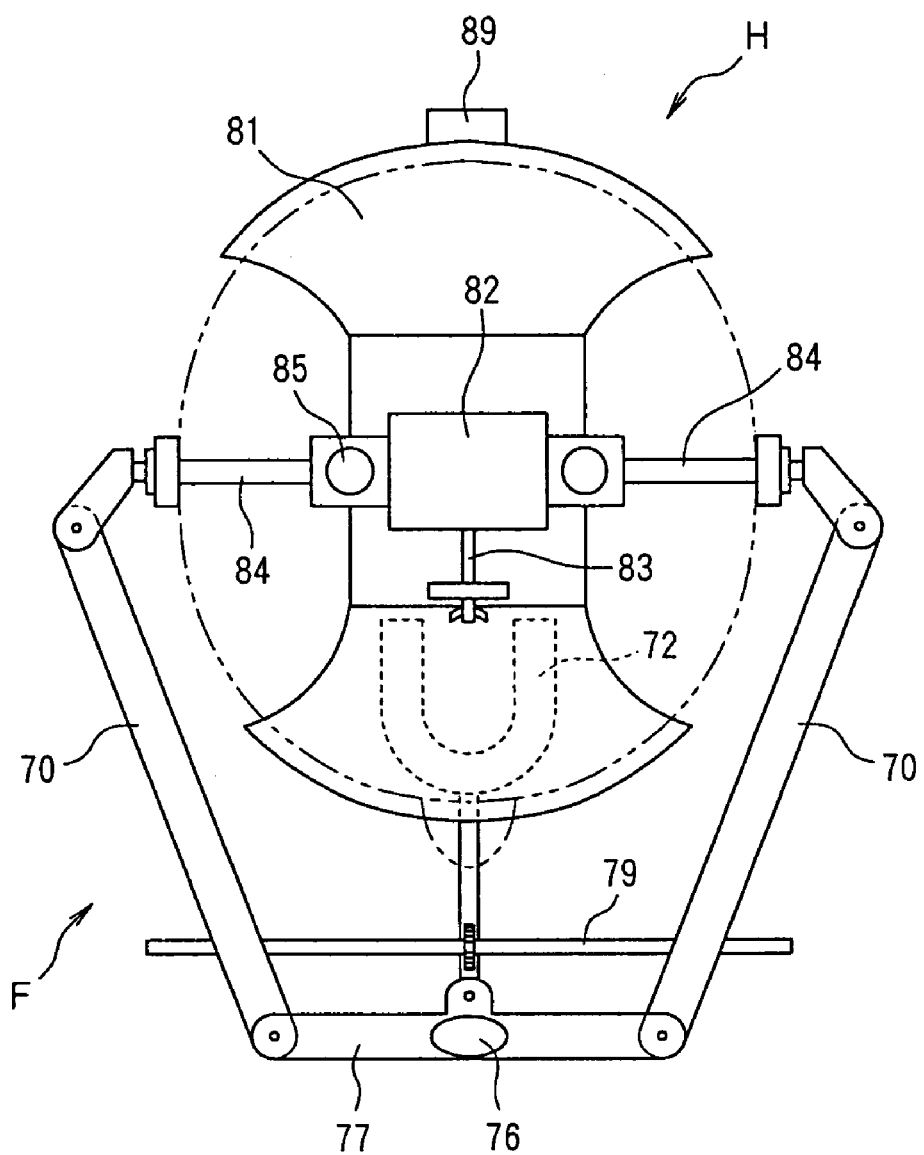
FIG. 16 is a plan view showing the relationship between the headgear and the face bow according to Embodiment 1 of the present invention.
Figure 17:
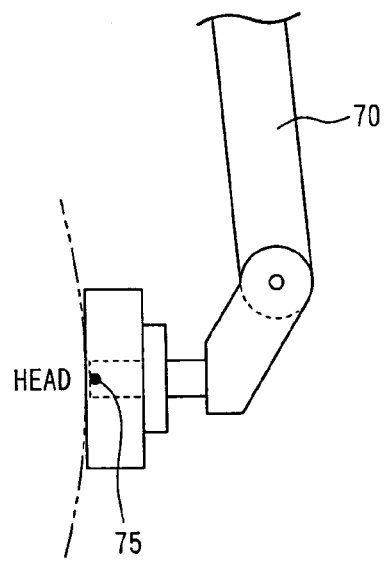
FIG. 17 is a partially enlarged view showing the relationship between the headgear and the face bow according to Embodiment 1 of the present invention.

Then, the face bow F is prepared. As shown in FIGS. 15 and 16, the ends of the right and left legs 70 are inserted respectively into the face bow F insertion holes 87 and make contact with a skin. Further, by adjusting the position of the nose piece 71 and readjusting the position of the head, the face bow F is adjusted so as to be leveled on a predetermined standard plane. At this point, the adjustment is made with reference to the level 76.

In the present specification, the horizontal plane (standard plane) where the face bow F is positioned may be referred to as a TYA plane. The TYA plane is a horizontal plane including the center of the right and left mandibular condyles of a patient or a position in the vicinity of the center. The standard plane for mounting the face bow F on the patient is not limited to the TYA plane. Conventional standard planes such as the Frankfurt plane (hereinafter, may be referred to as FH plane) and the Camper's plane may be used. Alternatively the face bow F may be mounted on a patient by using another plane as a standard plane. With the level 76 and the nose piece 71 whose position can be adjusted, it is possible to perform correct setting on the standard plane.

Subsequently, the X-ray CT device 40 is started while the above state is maintained, so that three-dimensional image data on the temporomandibular joint area is obtained.

Figure 18:
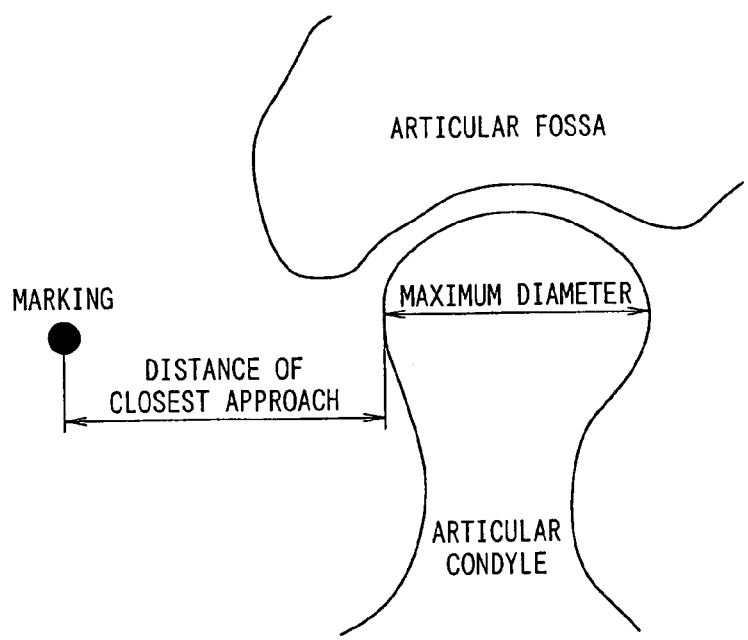
FIG. 18 is a front view showing the relationship between a marking member and a mandibular condyle according to Embodiment 1 of the present invention.

At this point, the marking members 75 disposed near the mandibular condyles are also arranged in the temporomandibular joint area and are photographed together. Therefore, it is possible to calculate a clearance (a distance of closest approach) between the mandibular condyle and the marking member 75 according to the coordinates of the contour of the mandibular condyle, the coordinates of a marking, and so on in the three-dimensional image data (see FIG. 18). The present embodiment comprises an approach distance arithmetic section 52. When the positions of the mandibular condyle and the marking member 75 are specified by clicking or the like in a tomogram on a display, the approach distance arithmetic section 52 calculates a distance between the mandibular condyle and the marking member 75 on the basis of the coordinates of the mandibular condyle and the marking member 75. Some functions of an arithmetic section 40D of the X-ray CT device 40 may be used as the approach distance arithmetic section 52.

Further, a distance between the right and left marking members is determined indirectly by a distance between the right and left face bow F mounting bodies 86 of the headgear H and directly by measuring a distance between the right and left markings of the face bow F.

Even at the completion of photographing in the X-ray CT device 40, the headgear H and the face bow F are kept as they are, an impression of the upper jaw is obtained using the bite fork 72, and the three-dimensional positional relationship between the temporomandibular joint and a maxillary occlusion plane is obtained.

Further, the three-dimensional image data serving as the arithmetic result is transmitted to the stereolithography machine 50 and stereolithography is performed on the basis of the three-dimensional image data, so that a solid model of the right and left mandibular joints is constructed.

In this case, the positions corresponding to the marking members 75 are laterally opposed to each other with respect to the center of the mandibular condyles. Thus, it is preferable to set the formation range during stereolithography while positioning the marking members 75 at the center of the height direction.

Then, the mandibular condyle model 14 and the maxillary fossa model 22 are mounted on the occludator K which are constituted of the solid model. Further, the lengths of the right and left bars 10, which are inserted into the insertion holes in the rear of the upper bow-shaped part 1, are adjusted in such a way that a distance between the vertical parts 8B of the right and left joint mounting parts 8 is equal to the previously determined distance between the right and left marking members 75.

Subsequently, the screw is turned in the forward/reverse direction to adjust the lateral positions of the articular condyle model 14 and the articular fossa model 22 in such a way that a distance between the adjacent vertical part 8B (or the marking member 75) and the articular condyle model 14 and the articular fossa model 22 is equal to the determined distance of closest approach.

Further, the spring 30 having a vertical axis is mounted. With the spring 30, it is possible to positively keep a contact between the mandibular condyle and the maxillary fossa, thereby reproducing a opening/closing movement and a lateral movement.

Figure 19:
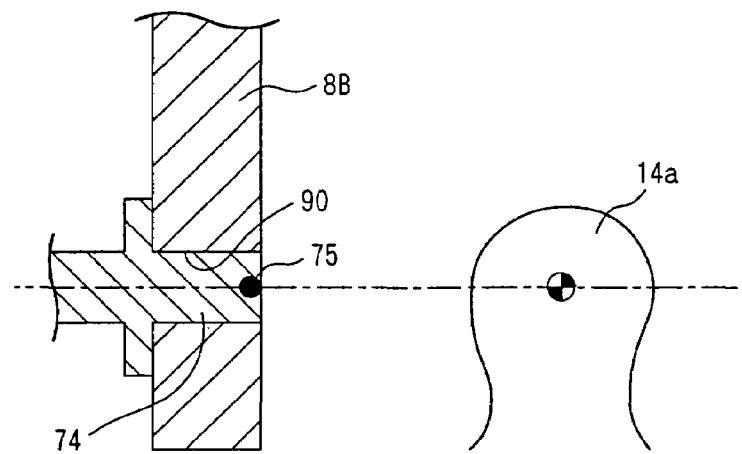
FIG. 19 is a front view showing the relationship between the marking member and a mandibular condyle model according to Embodiment 1 of the present invention.

In this case, as shown in FIGS. 1 and 19, a positioning hole 90, which permits the insertion of the insertion part 74 provided on the end of the face bow F, penetrates the right and left vertical part 8B on a position almost as high as the center of the condyle of the mandibular condyle model 14. In a state in which the insertion part 74 is inserted into the positioning hole 90, the marking member 75 is positioned almost on an opening end inside the positioning hole 90. The positioning hole 90 constitutes a connecting part on of the occludator.

Figure 20:
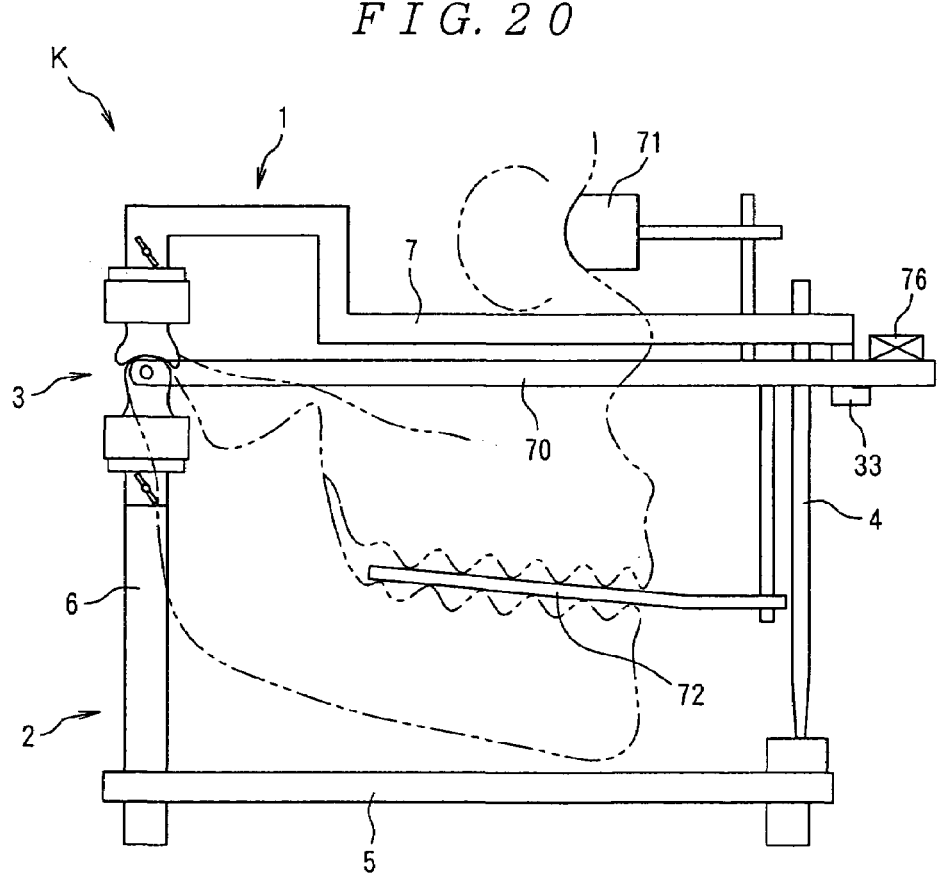
FIG. 20 is a side view showing the relationship between the occludator and the face bow according to Embodiment 1 of the present invention.
Figure 21:
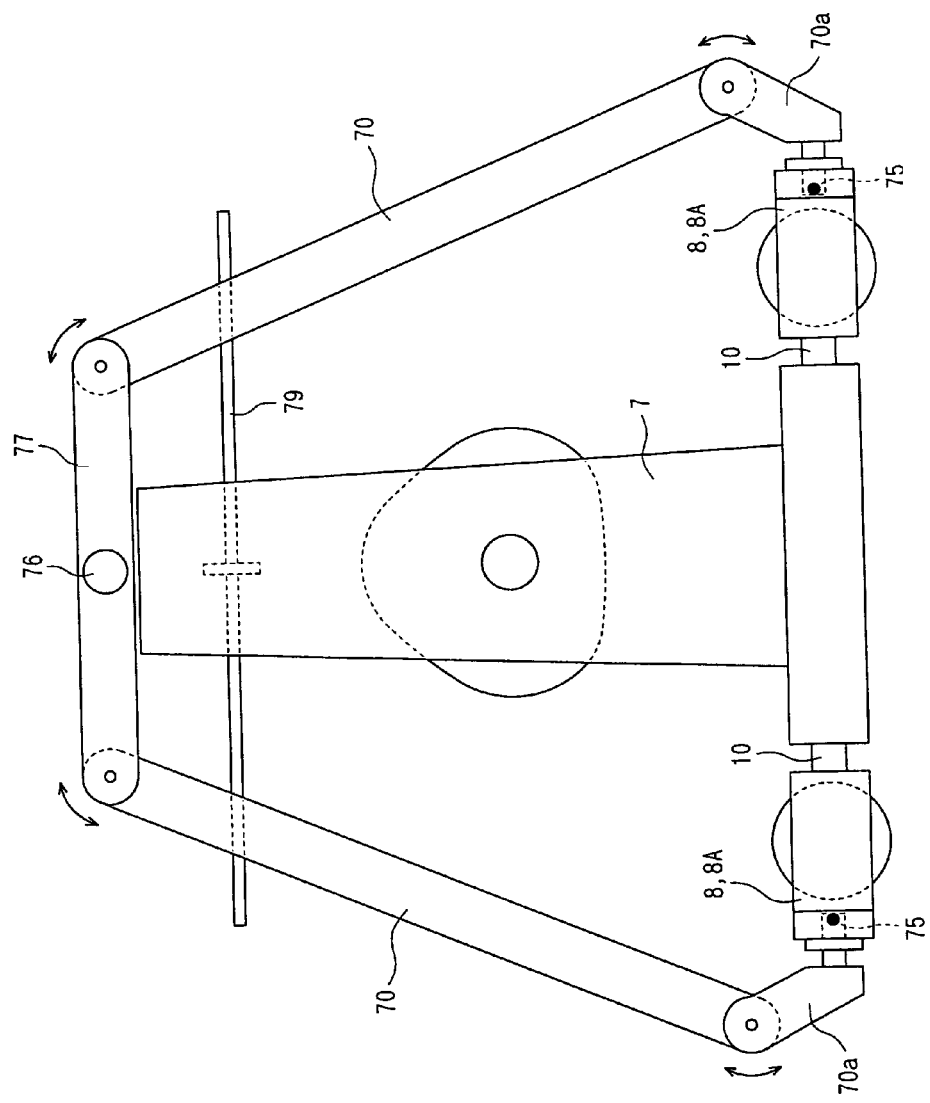
FIG. 21 is a plan view showing the relationship between the occludator and the face bow according to Embodiment 1 of the present invention.

Then, as shown in FIGS. 20 and 21, the face bow F having been used in photographing is mounted on the occludator K while being supported by the right and left positioning holes 90 and the catching part 33. At this point, an amount of protrusion of the incisal pin 4 from the upper bow-shaped part 1 is adjusted, so that the face bow F is leveled and is positioned on the TYA plane on the occludator K.

Subsequently, an upper jaw tooth mold is fixed on the washer of the upper bow-shaped part 1 with gypsum or the like. At this point, the upper jaw tooth mold is mounted on the washer of the upper bow-shaped part 1 while being positioned on a mark of the bite fork 72 mounted on the face bow F. Thereafter, a lower jaw tooth model is fixed on the washer of the lower bow-shaped part 2 so as to interpose a bite having recorded upper and lower occlusion.

Thus, the three-dimensional positional relationship between the occlusion plane and the right and left temporomandibular joints 3 in a living body is reproduced on the occludator K. That is, not only the structure of the temporomandibular joint of the patient, in which the structure of the joint 3 is the target, but also a distance between the right and left temporomandibular joints and the occlusion plane are reproduced by simple means on the same positions as three-dimensional positions in the living body.

In this way, in the system using the occludator K and the face bow F, the three-dimensional shapes of the right and left temporomandibular joints are reproduced on the occludator K according to the actual shapes of the temporomandibular joints of the patient. Further, a distance between the right and left temporomandibular joints and the occlusion plane are also reproduced on the occludator K with almost the same positional relationship as the living body.

That is, since a lower jaw movement (opening/closing movement, lateral movement, etc.) of the target patient can be reproduced in a three-dimensional manner, it is possible to achieve a technique for fabricating a crown prosthesis (crown and bridge), a partial dental plate, and a full denture most suitably for the patient.

Moreover, since occlusion unique to the patient can be reproduced, it is possible to obtain diagnoses and treatments of occlusion and develop treatment plans during diagnoses of improper occlusion and prostheses with higher accuracy.

Figure 22A:
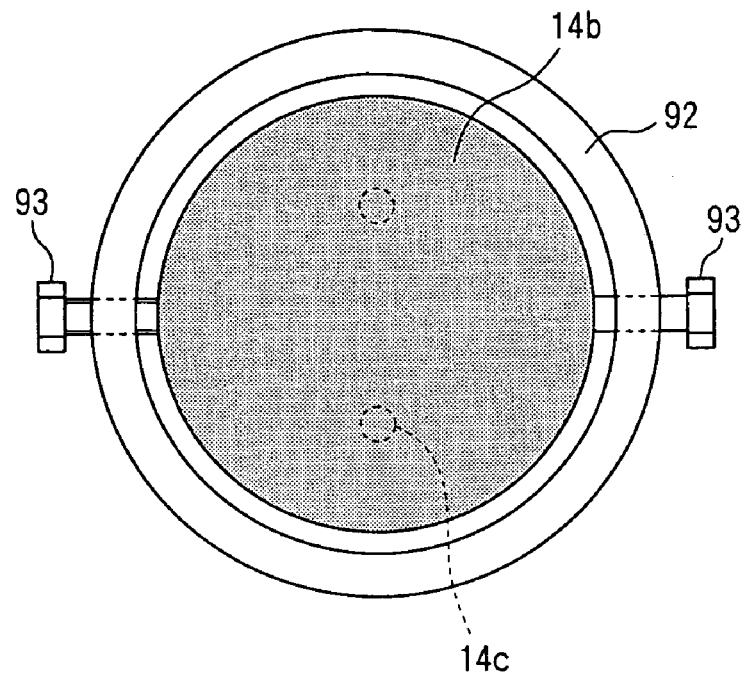
FIGS. 22A and 22B show another examples of the mounting of the model.
Figure 22B:
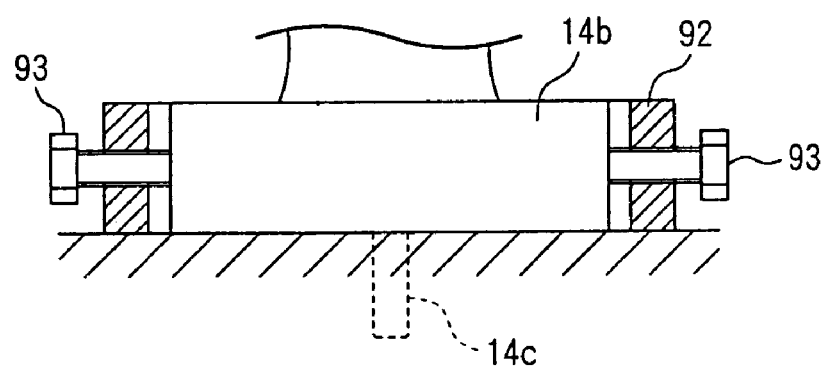
Figure 23:
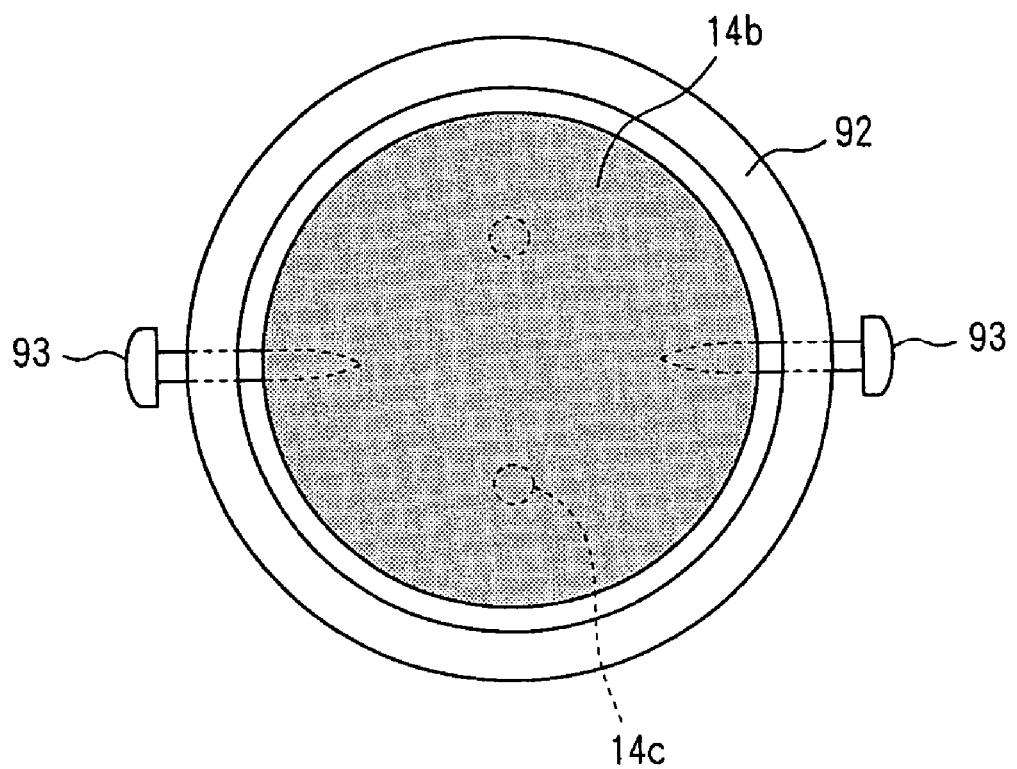
FIG. 23 is a plan view showing another example of the mounting of the model.

The present embodiment described the example where the models 14 and 22 are mounted by the mounting nuts 15 and 23. The configuration is not limited to the above. For example, as shown in FIGS. 22A and 22B, an end of the mounting member 13 has a ring-shaped part 92 which has a vertical axis and permits the insertion of the pedestal 14b of the solid model. The pedestal 14b of the solid model is inserted into a concave portion of the ring-shaped part 92, and the end of a screw 93 making a screwing connection is brought into contact with the ring-shaped part 92. Further, as shown in FIG. 23, the models 14 and 22 may be mounted by screwing into the pedestal 14b made of resin.

Figure 24A:
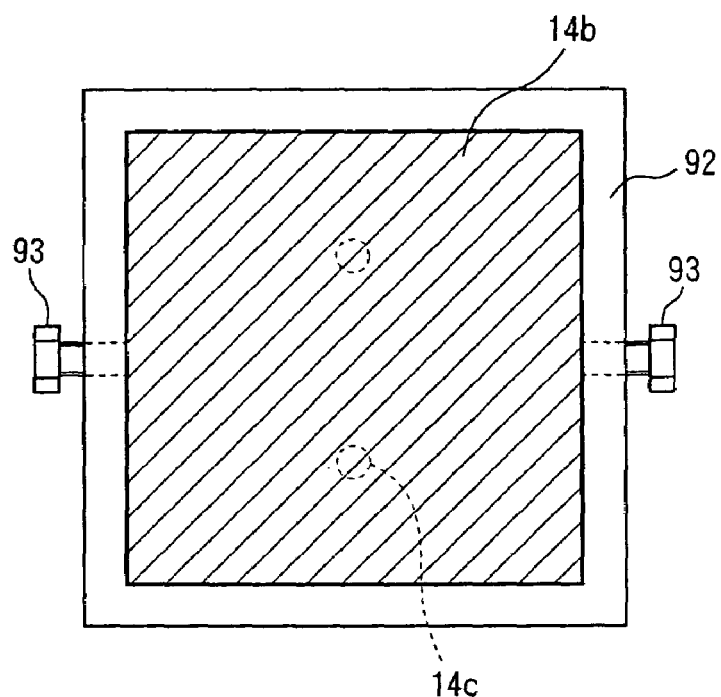
FIGS. 24A and 24B show another examples of the mounting of the model.
Figure 24B:
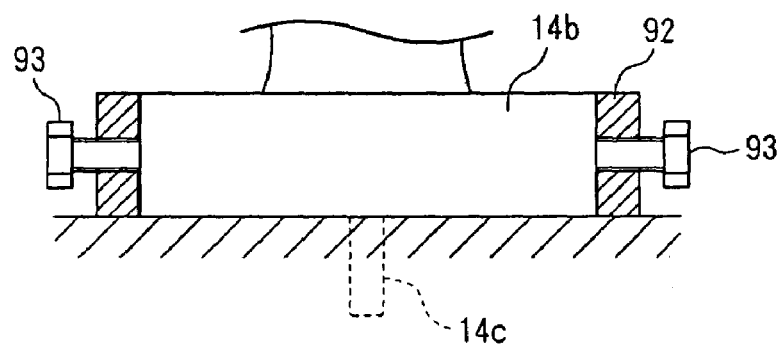

In this case, the configuration of FIGS. 24A and 24B are also applicable. FIGS. 24A and 24B show examples where the cross section of the pedestal 14b and the concave opening of the ring-shaped part 92 for the insertion of the pedestal 14b are both shaped like rectangles. Further, the pedestal 14b is shaped so as to be engaged into the concave portion of the ring-shaped part 92, that is, the pedestal 14b and the ring-shaped part 92 are similar in shape. The cross section and the opening are shaped like polygons such as a rectangle, so that positioning can be readily performed in a circumferential direction as well as the horizontal direction. Moreover, since the pedestal 14b is slightly elastic, the pedestal 14b may be fit into the concave portion of the ring-shaped part 92 while being tightened slightly. In this case, a fastening device such as the screw 93 is not always necessary.

In the present embodiment, the three-dimensional image data calculated by the X-ray CT device 40 is used as it is. The processing is not limited to the above.

Figure 39:
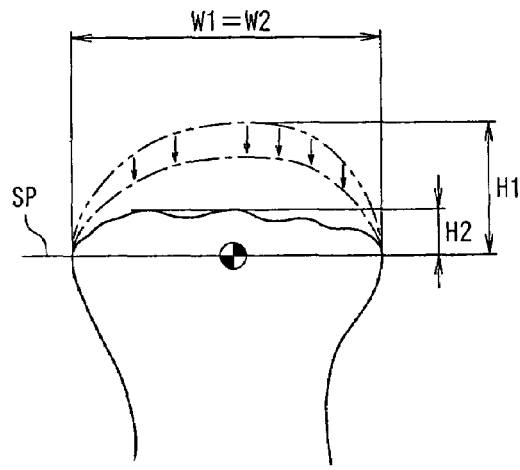
FIG. 39 is a diagram for explaining a correction example of the shape of the mandibular condyle.

For example, data correcting means may be provided for the following processing:

Regarding mandibular condyles, standard mandibular condyle model data serving as standard or ideal data is registered in a database for each predetermined category on the basis of three-dimensional image data or the like about a number of temporomandibular joints. First, on a specific cross-sectional image such as a longitudinal section image passing through the center of the condyle in front view, standard mandibular condyle model data on the database is selected on the basis of a predetermined classification criterion on the shapes of contours other than the protruding portion of the top. The model data is close to the three-dimensional image data having been calculated by the X-ray CT device 40. Subsequently, as shown in FIG. 39, a comparison is made between a ratio of a distance H1 to the top to a width W1 (calculated and stored beforehand) on a predetermined standard plane SP (e.g., a horizontal plane at the center of the condyle) of the mandibular condyle regarding the selected standard mandibular condyle model data (broken line), and a ratio of a distance H2 to the top to a width W2 on the predetermined standard plane for the three-dimensional image data (W1=W2 in FIGS. 24A and 24B and a difference may occur). When (H2/W2) is not larger than a predetermined value of (H1/W1), e.g., 0.6, it is decided that the protrusion of the top of the mandibular condyle wears out more than necessary in the three-dimensional data, and the three-dimensional image data is corrected such that the top of the mandibular condyle of the three-dimensional image data having been calculated by the X-ray CT device 40 is shaped like or close to the top of the standard model. In FIG. 39, a chain line shows an example of protrusion after correction. The protrusion is corrected to, e.g., 0.7 of the protrusion of the standard mandibular condyle. An amount of correction such as 0.7 may be inputted on the spot or automatically calculated on the basis of the ratios (H2/W2) and (H1/W1).

With this data correcting means, a condyle model close to a healthy condition is reproduced instead of a worn and distorted condyle, so that occlusion closer to a healthy condition than the present state is reproduced. Accordingly, prostheses can be fabricated and occlusion is treated.

Further, the following configuration is also applicable: two or more kinds (e.g., 256 kinds) of standard mandibular condyle model data and standard maxillary fossa model data are stored in the database according to the predetermined classification, selecting means is provided which selects standard mandibular condyle model data and standard maxillary fossa model data in the database that are close to the three-dimensional image data having been calculated by the X-ray CT device 40, stereolithography is performed using the standard mandibular condyle model data and standard maxillary fossa model data selected by the selecting means, and the mandibular condyle model 14 and the maxillary fossa model used in the occludator K are constructed.

In this case, it is possible to reduce the accuracy of three-dimensional data calculated by the X-ray CT device 40.

When the stereolithography machine 50 is disposed away from the X-ray CT device 40, three-dimensional image data calculated by the X-ray CT device 40 has to be transmitted through a communication device such as the Internet in the present embodiment, resulting a large amount of transmission data. In this processing method, both of the X-ray CT device 40 and the stereolithography machine 50 are provided with the databases, so that only identification information about the number or the like of the standard model has to be transmitted through the communication device. Thus, it is possible to considerably reduce an amount of data to be transmitted.

Moreover, the following configuration is also applicable: models are prepared according to the standard mandibular condyle model data and standard maxillary fossa model data in the database (the model does not have to be made of resin), selecting means is provided which selects standard mandibular condyle model data and standard maxillary fossa model data in the database that are close to the three-dimensional data having been calculated by the X-ray CT device 40, and a model selected by the selecting means is extracted from prepared models and is mounted and used on the occludator K.

In this case, the stereolithography machine 50 is unnecessary.

In a classification example of standard model data registered in the database, for example, classification and registration are performed by four parameters of a frontal shape, a side shape, a top shape, and a size of a cross-sectional image passing through the center of the condyle, and data close to the three-dimensional data calculated by the X-ray CT device 40 is automatically selected according to the classification. As a matter of course, classification is not limited to the above. Characteristics of the contours of other maxillary fossas and mandibular condyles may be extracted and classification may be performed on the basis of the characteristics. Various kinds of matching techniques can be used to decide whether data is close or not. Simply, a model to be used may be selected from two-dimensional X-ray radiographs.

Further, in this embodiment, data is transmitted from the X-ray CT device 40 to the stereolithography machine 50 through a communication device such as an Internet device. The following transmission is also applicable: the three-dimensional image data calculated by the X-ray CT device 40 is divided into a plurality of two dimensional image data along the Z axis for stereolithography in the X-ray CT device 40, and then the plurality of two-dimensional image data is transmitted to the stereolithography machine 50. In this case, even two-dimensional data results in a large amount of transmission data. Thus, groups of two or more coordinates for specifying each corresponding contour of the two-dimensional image data may be transmitted instead of the two-dimensional image data. This processing can considerably reduce an amount of transmission data.

In this embodiment, both of the mandibular condyle model 14 and the maxillary fossa model 22 correspond to the outer contours of the temporomandibular joints of a target patient. Models are not limited to the above. For example, one of the models 14 and 22 may be a general-purpose model (identical only in size to the other).

In this embodiment, the coil spring was described as an example of an elastic body. A material such as rubber is also applicable and the installation position is not limited to the above. In short, at least the mandibular condyle model 14 and the maxillary fossa model 22 have to be vertically brought into contact with each other via the elastic body. An urging state close to a standard or ideal urging state of muscle in a living body may be reproduced on the occludator by arranging the position of the elastic body.

Further, by using the solid model prepared by stereolithography, an artificial joint for a temporomandibular joint may be formed by a biocompatible material, e.g., titanium and ceramics. For a person who has broken a joint or extracted a joint due to a disease, a joint unique to the person can be restored or the most suitable shape for a maxillary fossa can be provided.

A supplementary explanation will be given on stereolithography based on the three-dimensional image data having been photographed and calculated by the X-ray CT device 40.

Although forming may be performed over the photographing area of the X-ray CT device 40 as a forming area of stereolithography, the photographing area may be displaced, that is, may be varied according to the technique of the photographer as shown in FIGS. 40 to 43, so that the position of a joint may be different for each product. Moreover, three-dimensional data has to be calculated uselessly. In FIGS. 40 to 43, reference character A denotes an image pickup area, reference character B denotes the forming area, and reference character C denotes an imaged target or imaging center.

Figure 40:
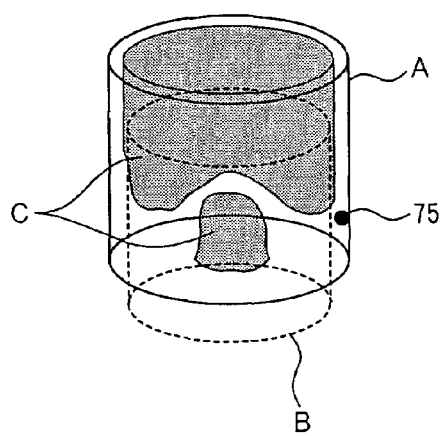
FIG. 40 is a schematic diagram showing the relationship between an image pickup area and a forming area.
Figure 41:
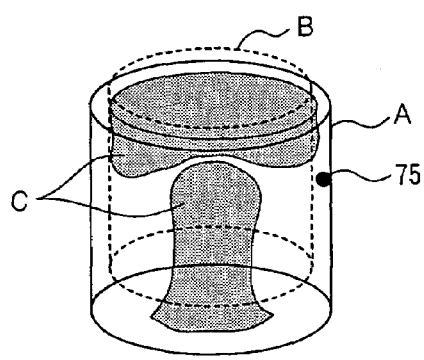
FIG. 41 is a schematic diagram showing the relationship between the image pickup area and the forming area.

For this problem, in the present embodiment, the marking member opposed to the center of the mandibular condyle from the side is photographed together with a joint part, so that the forming area B can be positioned as follows:

First, as described above, the position corresponding to the marking member 75 is laterally opposed to the center of the mandibular condyle. Thus, the forming area B during stereolithography is set while the marking member 75 is positioned at the center of the height direction. Hence, as shown in FIGS. 40 and 41, the center of the upper and lower solid models can be set at the center of the forming area B. As a result, when the solid model is mounted on the occludator, the center of the mandibular condyle of the solid model can be aligned with a position laterally opposed to the marking member of the face bow F connected to the occludator.

Figure 44:
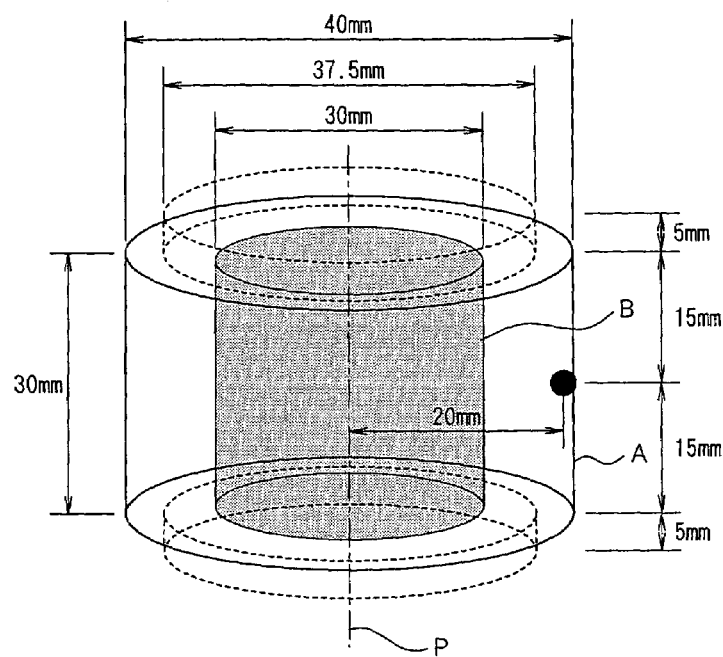
FIG. 44 is a schematic diagram showing the relationship between the image pickup area and the forming area.

Further, the size of the forming area B is determined according to the position of the marking member, thereby minimizing the forming area B. For example, when the position of the marking member is set so as to make contact with a skin of a patient, the center of the mandibular condyle is generally positioned about 20 mm inside the marking member. Therefore, in this case, as shown in FIG. 44, a cylinder around a vertical axis P serves as the forming area B. The vertical axis P is positioned 20 mm inside along the lateral direction from the marking member. The cylinder is 15 mm in radius and is higher or smaller than the marking member by 15 mm, that is, 30 mm in height. The shaped pedestal is added vertically to the cylinder. Numbers on the image pickup area A of FIG. 44 are just examples and are varied with the size of a standard temporomandibular joint.

Figure 42:
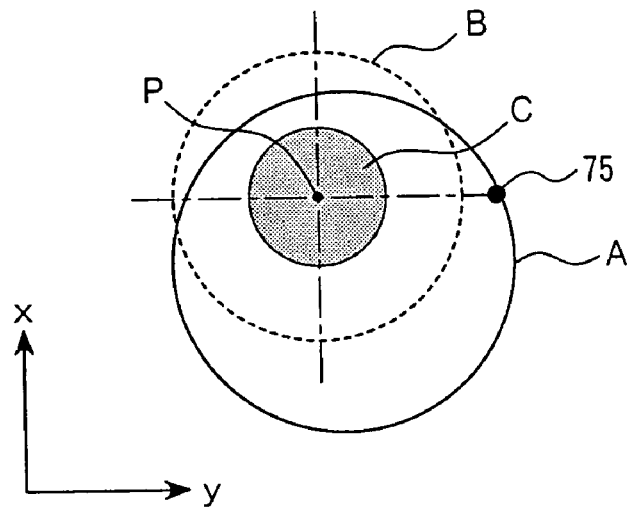
FIG. 42 is a schematic diagram showing the relationship between the image pickup area and the forming area.
Figure 43:
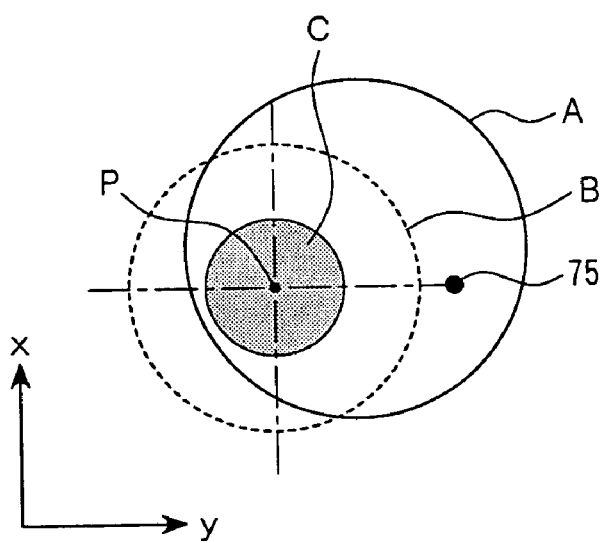
FIG. 43 is a schematic diagram showing the relationship between the image pickup area and the forming area.

Reference character A in FIG. 44 denotes an ideal photographing area. On the assumption that the photographing area A is cylindrical, the photographing area and the forming area B should be concentric circles in plan view (view from the top). However, as shown in FIGS. 42 and 43, the center of the photographing area and the area center of the imaged target C (a part passing through the center of the mandibular condyle) are readily displaced from each other as described above. In contrast, as described above, the center of the forming area B is specified and is used as a standardized area relative to the marking member, so that even when the photographing area is displaced, forming can be performed while the center of the forming area B is aligned with the area center of the imaged target C.

Moreover, the three-dimensional image data photographed and calculated by the X-ray CT device 40 includes noise, such as floating noise, unique to a living body and other kinds of noise. Thus, when the three-dimensional data is used for forming as it is, a formed three-dimensional object has less accurate contours.

For this reason, this embodiment presents a processing method as an example of noise processing, in which expansion is temporarily performed into a plurality of two-dimensional images in a multidirectional manner, noise is reduced and the contour of an object is extracted for each of the two-dimensional images, and then the images are rearranged in a three-dimensional manner.

Further, the maxillary fossa is disposed so closely as to cover the mandibular condyle from above and thus the mandibular condyle model and the maxillary fossa model may not be separated well. Hence, instead of or in parallel with the first noise processing, it is preferable to perform second and third noise processing (described below) on the three-dimensional data.

The second noise processing is a processing method of labeling the vertical consecutiveness of pixels in the image pickup area A of the three-dimensional data and removing inconsecutive pixels as floating noise. For example, pixels on the underside of an image area are labeled and labeling is performed between the labeled pixels and an array, which is one stage above the pixels, so that a continuous area (surface) is specified. This processing is performed to the top face of the image area, and the pixel value of an unlabeled pixel is set at 0 and removed. This processing is also performed from the top face to the underside of the image area. Hence, even from an object shaped like a letter "J," floating noise components can be removed.

Figure 45A:
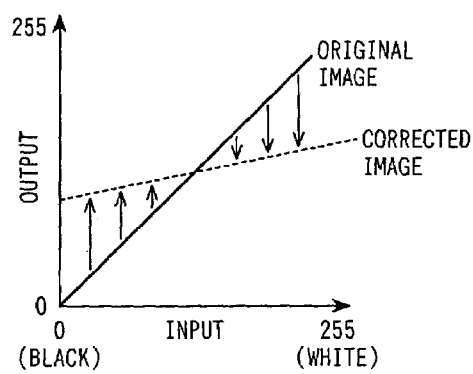
FIGS. 45A and 45B are diagrams for explaining a correction of a concentration.
Figure 45B:
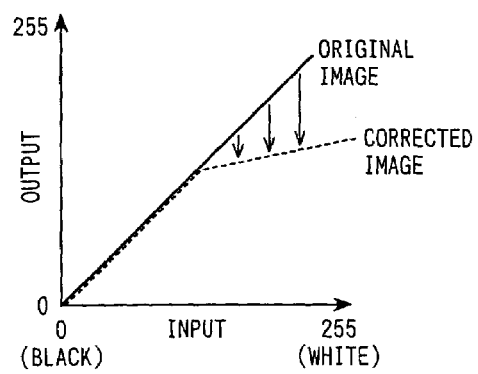

In the third noise processing, noise components are removed by properly changing, for each pixel, a parameter for correcting a concentration, so that a boundary of a temporomandibular joint is sharpened. That is, a threshold value Th (e.g., Th=α×A:0<α<1) is determined by an average pixel value A of the obtained three-dimensional data, an average A1 of the number of pixels around a target pixel is determined for each target pixel, and a concentration of the target pixel is corrected according to a difference between A1 and the threshold value Th. For example, as shown in FIGS. 45A and 45B, (A=Th), a brightness relatively decreases in a pixel where brighter than the threshold value and a brightness relatively increases in a pixel where darker than the threshold value. That is, a concentration of each pixel is corrected according to information about the vicinity of the target pixel relative to information about the overall image. Thus, in a part where a color continuously changes, a somewhat faint color appears and noise is reduced. Conversely, in a part where a contrast rapidly changes, that is, on a boundary of the joints, colors are sharpened. It was confirmed that this processing removes noise components and a boundary of temporomandibular joints is sharpened.

Embodiment 2 will be described below in accordance with the accompanying drawings. The same components as the above-described embodiment will be indicated by the same reference numerals and characters.

The basic configuration of Embodiment 2 is similar to that of Embodiment 1. A face bow F and a part of an occludator that corresponds to the face bow F are different from those of Embodiment 1.

First, the configuration of the face bow F of the present embodiment will be discussed below.

Figure 25:
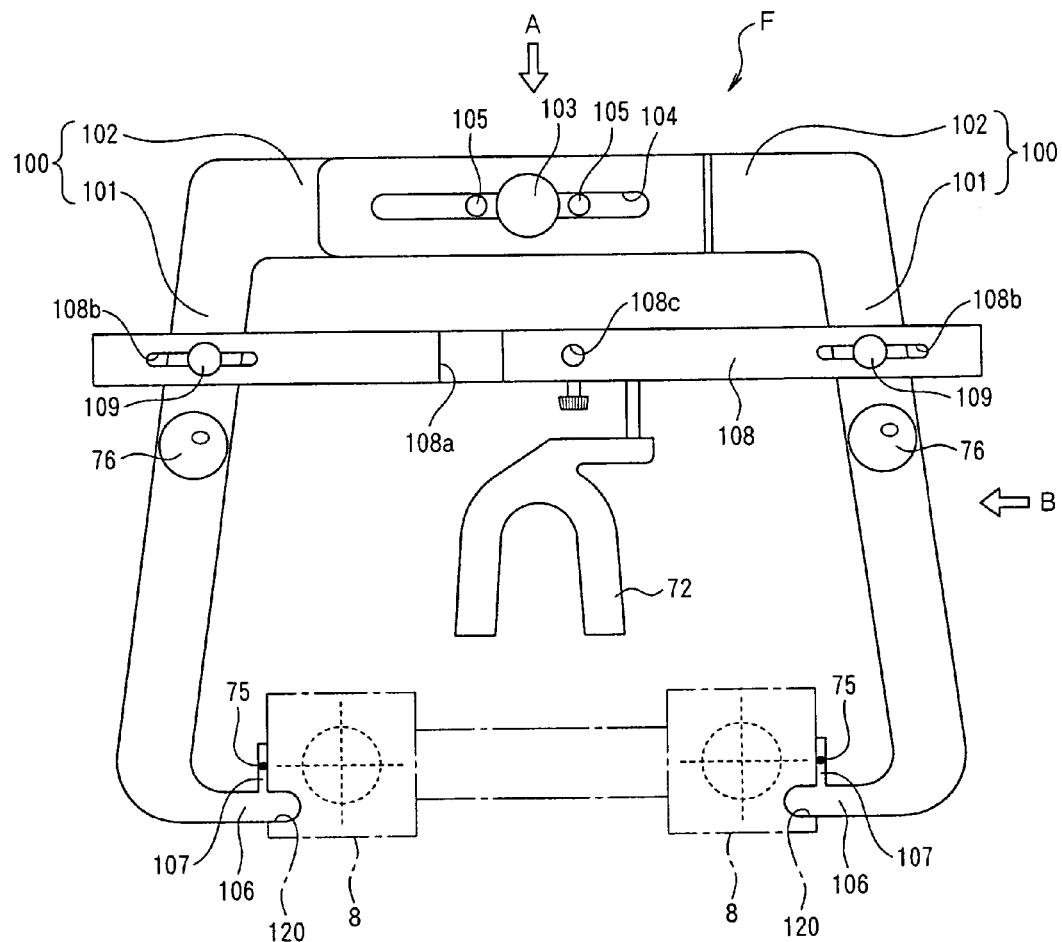
FIG. 25 is a plan view showing a face bow according to Embodiment 2 of the present invention.
Figure 26:
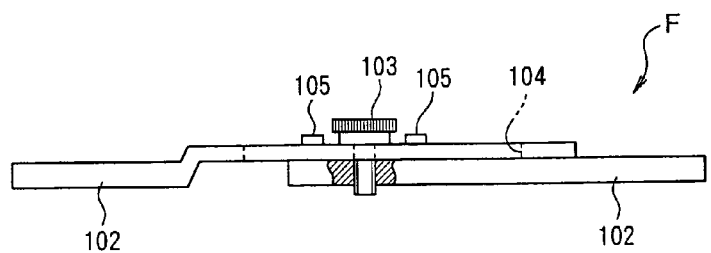
FIG. 26 is a diagram taken from arrow A of FIG. 25.
Figure 27:
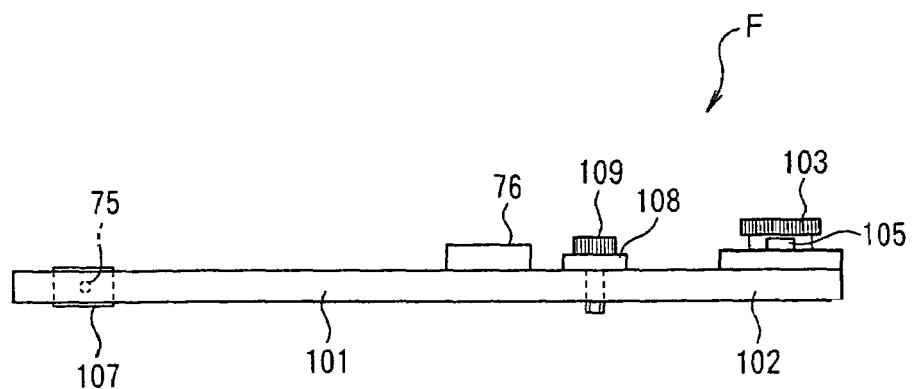
FIG. 27 is a diagram taken from arrow B of FIG. 25.

As shown in FIGS. 25 to 27, in the body of the face bow F, legs 100 on the right and left are symmetrically opposed to each other. Each of the legs 100 is shaped like a letter L in plan view. The leg 100 is constituted of a leg body 101 which stretches to the front and rear and a platy horizontal part 102 which is connected to the base of the leg body 101 and stretches to the other opposed leg 100.

As shown in FIG. 26, the right and left horizontal parts 102 are vertically overlaid on the other so as to slide in the lateral direction. The upper horizontal part 102 has a long opening 104 stretching in the lateral direction, and the lower horizontal part 102 has a tapped hole which can be screwed to the axis of a fastening screw 103 penetrating the long hole 104. The fastening screw 103 is loosened, an amount of overlapping of the right and left horizontal parts 102 (a distance between the right and left leg bodies 101) is adjusted, and then the fastening screw 103 is tightened again for fixing.

Reference numeral 105 denotes two protrusions which protrude from the lower horizontal part 102 into the long opening 104. When the horizontal parts 102 are slid by loosening the fastening screw 103, the protrusions regulate the two horizontal parts 102 so as to have a slide only in the lateral direction. Moreover, the regulating mechanism permitting only lateral sliding is not limited to the above. A known linear guide mechanism and so on are also applicable.

As described above, although the right and left horizontal parts 102 are partially overlaid on the other in the vertical direction, the right and left leg bodies 101 are positioned on the same plane by a step.

Ear rods 106 to be inserted into the external auditory meatuses of a patient are provided on the ends of the right and left leg bodies 101. A platy or stick-like protrusion 107 is provided which protrudes from a midpoint of the ear rod 106 to the front. A marking member 75 is provided on the protrusion 107. The marking member 75 is set on a position presumed to be laterally opposed to the center of a mandibular condyle. For example, when the standard plane of the face bow F is the FH plane, the marking member 75 is preferably positioned about 12 mm forward from the center of the ear rod 106. Also when other standard planes are used, according to the standard plane used by the face bow F, the position of the marking member 75 relative to the ear rod 106 is set on a position presumed to be opposed to the center of the mandibular condyle. The marking member 75 is made of a material not permitting the passage of X-ray beams, e.g., a stainless or aluminum ball.

The position of the marking member 75 may be slid to the front and rear. In this case, it is preferable to accordingly slide the position of an ear rod hole 120 of the occludator to the front and rear.

Figure 28:
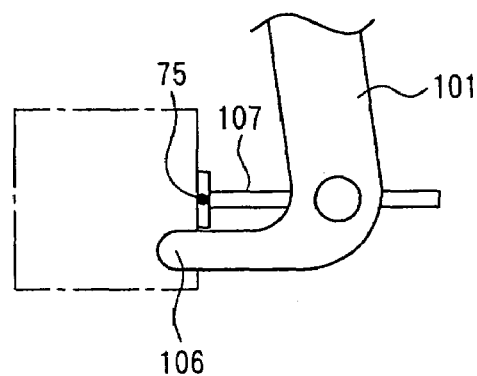
FIG. 28 is a diagram showing another example of a protrusion 107.

In this case, as shown in FIG. 28, the protrusion 107 for supporting the marking member 75 may laterally protrude from the leg body 101. FIG. 28 illustrates an example where the protrusion 107 is supported so as to slide in the lateral direction with respect to the leg body 101.

Further, a horizontal bar 108 is disposed across the right and left leg bodies 101 in parallel with the horizontal parts 102. The horizontal bar 108 is connected so as to move laterally relative to the leg bodies 101. In the present embodiment, long openings 108*b* stretching in the lateral direction are formed in the horizontal bar 108 so as to face the leg bodies 101. The shaft of a screw 109 penetrating the long opening 108*b* is screwed into a tapped hole formed in the leg body 101.

A bite fork 72 and a nose piece (not shown in FIG. 25) are mounted on the horizontal bar 108. Reference numeral 108*a* denotes the mounting portion of the nose piece.

Further, a level 76 is mounted on each of the leg bodies 101.

Figure 29:
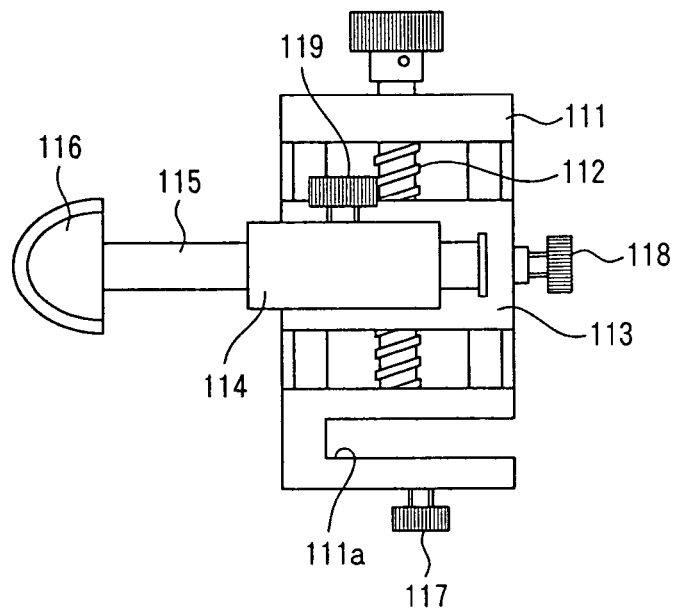
FIG. 29 is a diagram showing a nose piece.
Figure 30:
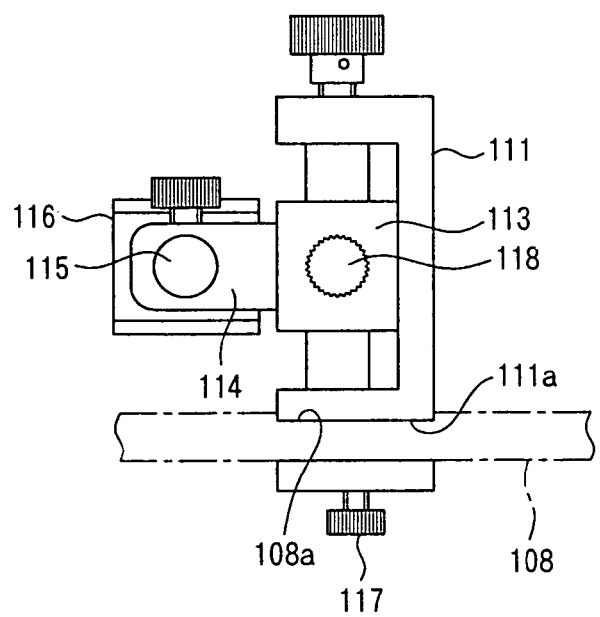
FIG. 30 is a diagram showing that the nose piece is mounted on a horizontal bar.

The following will describe the mounting of the nose piece onto the horizontal bar 108. As shown in FIGS. 29 and 30, there are provided: a column 111 which has a fit portion 111*a* and stretches upward, the fit portion 111*a* being fit and mounted onto the horizontal bar 108 from the front or rear, a screw rod 112 which has a vertical shaft whose upper and lower ends are supported by the column so as to freely rotate, and a slider 113 composed of a nut member which is screwed to the screw rod 112 and is vertically displaced by the rotation of the screw rod 112. The slider 113 is guided by the column 111 so as to move only in the vertical direction.

A cylindrical member 114 which has a longitudinal axis and a through hole is supported by the slider 113. A nose piece body 116 is provided on an end of a rod 115 which vertically penetrates the cylindrical member 114. This mechanism constitutes a position adjusting mechanism.

Reference numeral 117 denotes a screw for fixing onto the horizontal bar 108 of the column, reference numeral 118 denotes a screw which is screwed into the slider 113, brings an end of the shaft into contact with the screw rod 112, and fixes the position of the slider 113, and reference numeral 119 denotes a screw which brings an end of the shaft in contact with the rod 115 and fixes the rod 115 to the cylindrical member 114.

Further, the level 76 is mounted on each of the leg bodies 101.

The legs 100 and the protrusions 107 are made of a radiolucent material and a material of a predetermined strength, e.g., duralumin, an acrylic sheet, a baking plate, fiber reinforced plastics, and so on. A transparent material is more preferable.

Although the basic configuration of the occludator is similar to that of Embodiment 1, the ear rod holes 120 for inserting the ear rods 106 of the face bow F are provided instead of the positioning holes 90 enabling the insertion of the insertion parts 74. The ear rod holes 120 constitute a connecting part of the occludator. As shown in FIG. 25, the ear rod hole 120 is formed 12 mm backward from a position corresponding to the center of the mandibular condyle, that is, a position where the positioning hole is formed. As a result, when the ear rods 106 are inserted into the ear rod holes 120, the position of the marking member 75 is laterally opposed to the position corresponding to the center of the mandibular condyle.

Figure 31:
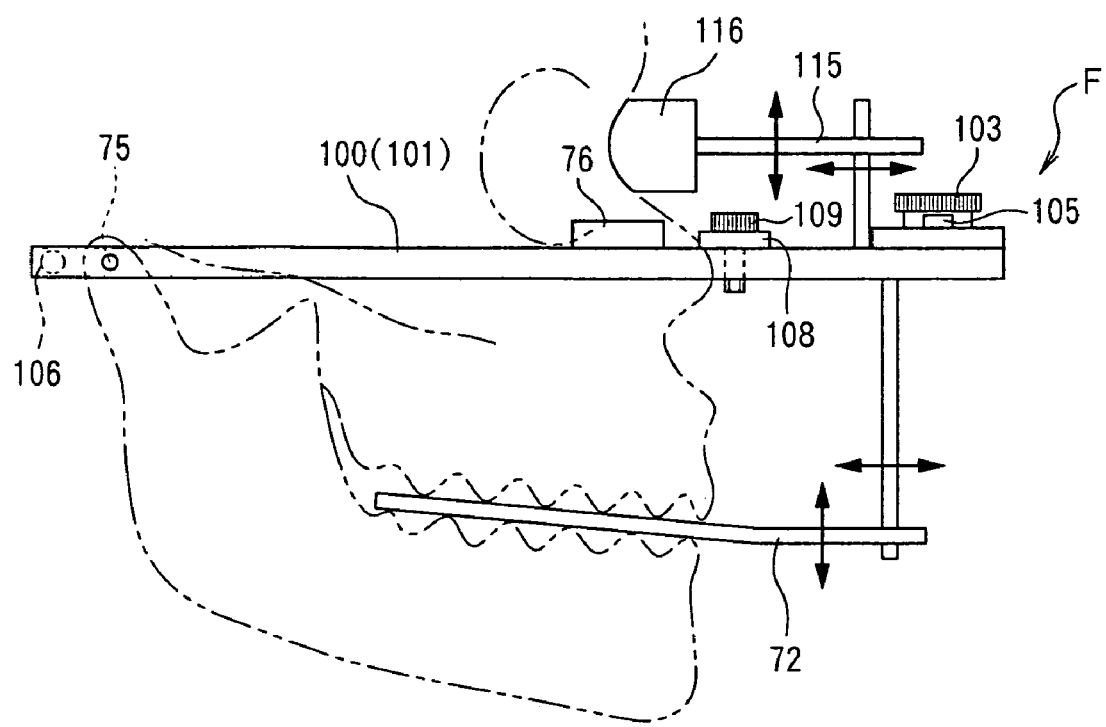
FIG. 31 is a schematic diagram showing the relationship between a head and the face bow.

Then, as shown in FIG. 31, the right and left ear rods 106 of the face bow F are inserted into the right and left external auditory meatuses of a patient until the protrusions 107 make contact with a skin, and a distance between the right and left leg bodies 101 is adjusted, and then the fastening screw is tightened to combine the right and left legs 100. Thereafter, the nose piece member is mounted on the horizontal bar 108, the nose piece member and the head position of the patient are adjusted so as to level the upper face of the face bow F on the FH plane, and then the screws are tightened for fixing. At this point, the degree of levelness of the face bow F is confirmed by the right and left levels 76.

Subsequently, photographing is performed by an X-ray CT device 40 in the above-described manner and a solid model is constructed by stereolithography. The face bow F is kept as photographed.

Then, the solid model is mounted on the occludator in the same manner as Embodiment 1.

Figure 32:
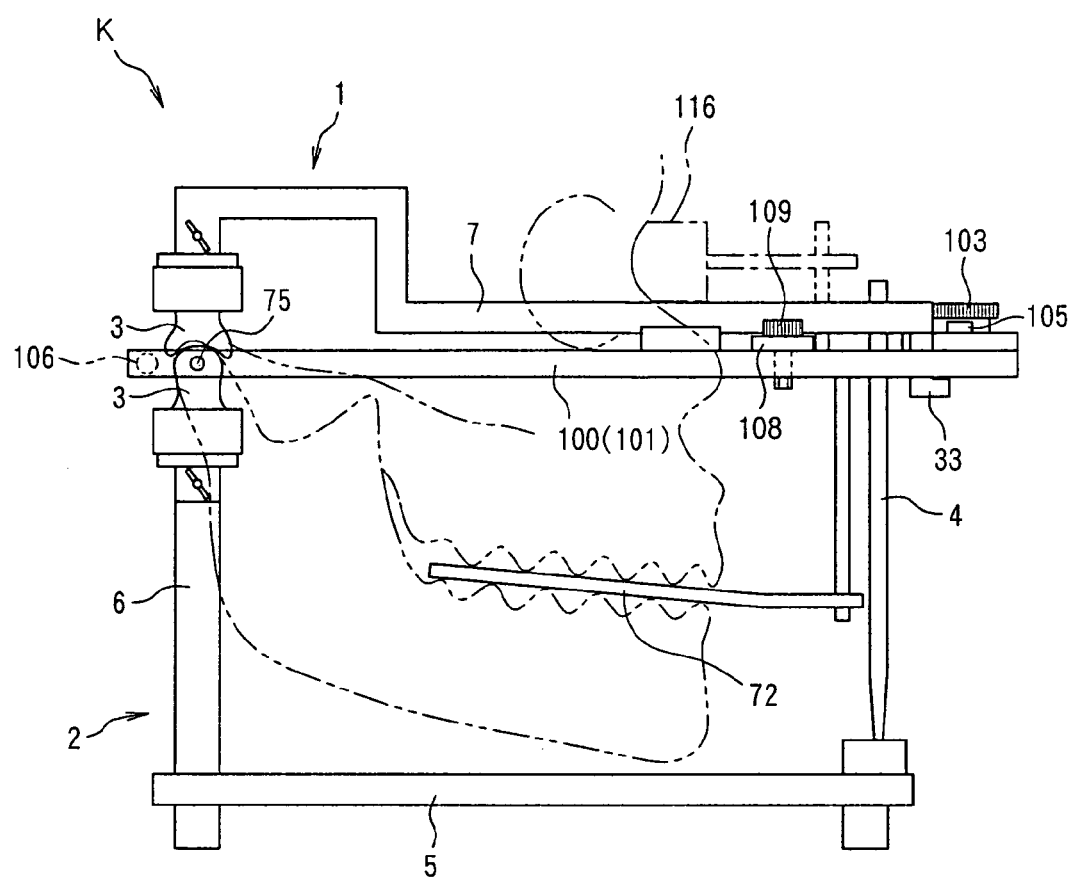
FIG. 32 is a schematic diagram showing a connection of the face bow and the occludator.

Subsequently, as shown in FIG. 32, the ear rods 106 of the kept face bow F are inserted into the ear rod holes 120 of the occludator to connect the face bow F to the occludator. The nose piece is detached beforehand.

While the degree of levelness is confirmed by the levels 76 of the face bow F, a length of an incisal pin is adjusted to level the face bow F.

Then, an upper jaw tooth mold whose impression has been obtained is mounted on an upper bow-shaped part. Further, a material is interposed where occlusion has been obtained to form upper and lower prostheses, and a lower jaw tooth mold is mounted while occluding to the upper jaw tooth mold.

In the case of the face bow F of the present embodiment, a headgear is unnecessary during photographing. Further, the face bow F can be more readily set on the standard plane with high accuracy and an occlusion plane and so on can be positively copied to the occludator.

In the present embodiment, the position of the nose piece relative to the face bow F is adjusted, so that the face bow F can be positioned and adjusted more positively on three points of the head of the patient. Thus, it is possible to align the face bow F with the standard plane (FH plane in the present embodiment) with higher accuracy. Moreover, the degree of levelness can be confirmed more positively by the levels 76.

The standard plane is not limited to the FH plane. Other planes can act as the standard plane without any problems.

Other configurations and operations/working effects are similar to those of Embodiment 1.

Embodiment 3 will be described below in accordance with the accompanying drawings. The same members as the above-described embodiments will be indicated by the same reference numerals and characters.

The basic configuration of Embodiment 3 is similar to that of Embodiment 2. A face bow F is different from that of Embodiment 2.

Figure 33:
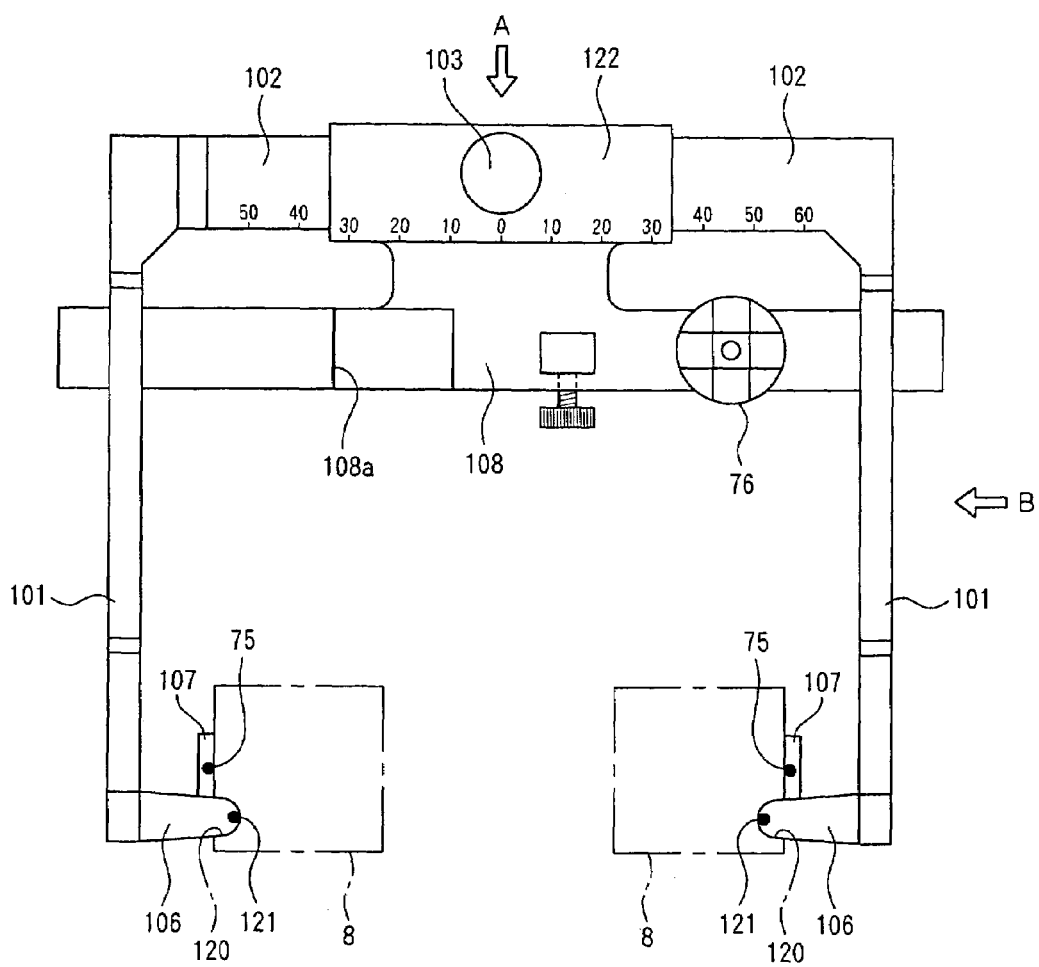
FIG. 33 is a plan view showing the face bow according to Embodiment 2 of the present invention.
Figure 34:
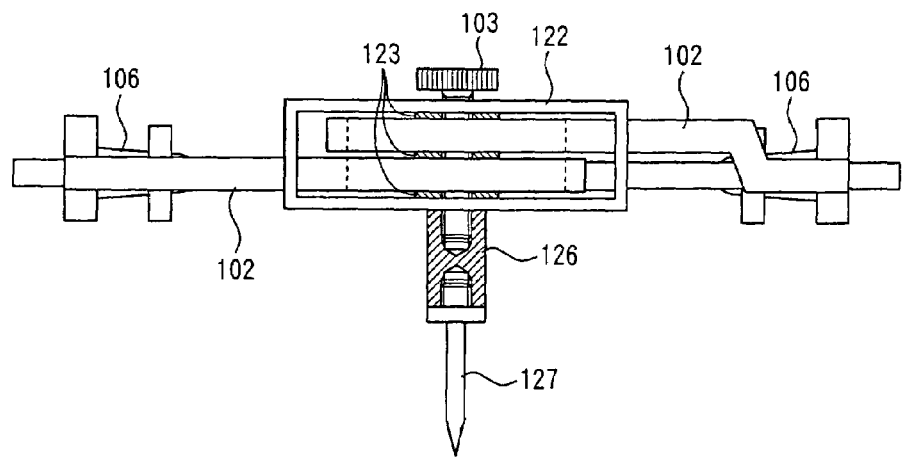
FIG. 34 is a diagram taken from arrow A of FIG. 33.
Figure 35:
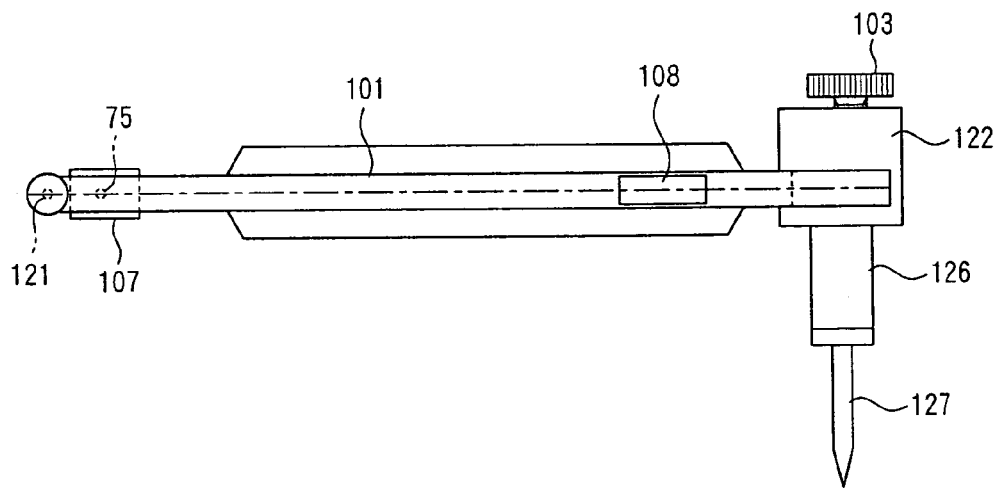
FIG. 35 is a diagram taken from arrow B of FIG. 33.

Referring to FIGS. 33 to 35, the face bow F of the present embodiment will be discussed below.

As with Embodiment 2, right and left legs 100 of the present embodiment are shaped like letters L in plan view, and right and left horizontal parts 102 are vertically overlaid on the other. However, in the present embodiment, a long opening stretching in a lateral direction is formed in each of the horizontal parts 102. The horizontal parts 102 are guided by a box 122 so as to move only in the lateral direction. The top plate and the bottom plate of the box 122 have tapped holes in positions vertically opposed to the long openings formed in the horizontal parts 102. A fastening screw 103 penetrates the upper and lower tapped holes and the long openings of the horizontal parts 102 from above and is screwed into a nut member 126 below. A washer 123 is interposed between the top plate of the box and the upper horizontal part 102, between the upper and lower horizontal parts 102, and between the lower horizontal part 102 and the bottom plate of the box. Then, in a state in which the fastening screw 103 is loosened, the right and left legs 100 are symmetrically displaced and positioned, and then the fastening screw 103 is tightened again. Thus, a distance between the right and left leg bodies 101 is adjusted.

The nut member 126 has a vertical axis. An upper tapped hole for screwing the fastening screw is formed in the upper side of the nut member 126, and a lower tapped hole for mounting a center positioning pin 127 is formed in the bottom of the nut member 126. The center positioning pin 127 is a rod having a vertical axis. The top of the center positioning pin 127 has a male screw screwed into the lower tapped hole.

Further, in the present embodiment, a horizontal bar 108 for mounting a bite fork and a nose piece is fixed on the box 122. The right and left ends of the horizontal bar 108 penetrate the leg bodies 101, respectively. Thus, the right and left leg bodies 101 can slide laterally with respect to the horizontal bar 108. Reference numeral 108a denotes the mounting portion of the nose piece.

Moreover, in the present embodiment, marking members 121 are provided also on the ends of ear rods 106. Besides, a level 76 is mounted on the horizontal bar 108.

In the face bow F of the present embodiment, the right and left ear rods 106 are inserted and mounted into the right and left external auditory meatuses of a patient, the face bow F is set so as to be positioned on a standard plane such as the FH plane, and an impression is obtained.

At this point, in the present embodiment, the center positioning pin 127 enables an inclination of a face to be recognized visually, thereby readily adjusting an inclination of a face and so on. When the face bow F is mounted on the occludator, the center positioning pin 127 is unnecessary and thus removed. The center positioning pin 127 may be used instead of an incisal pin.

Figure 36:
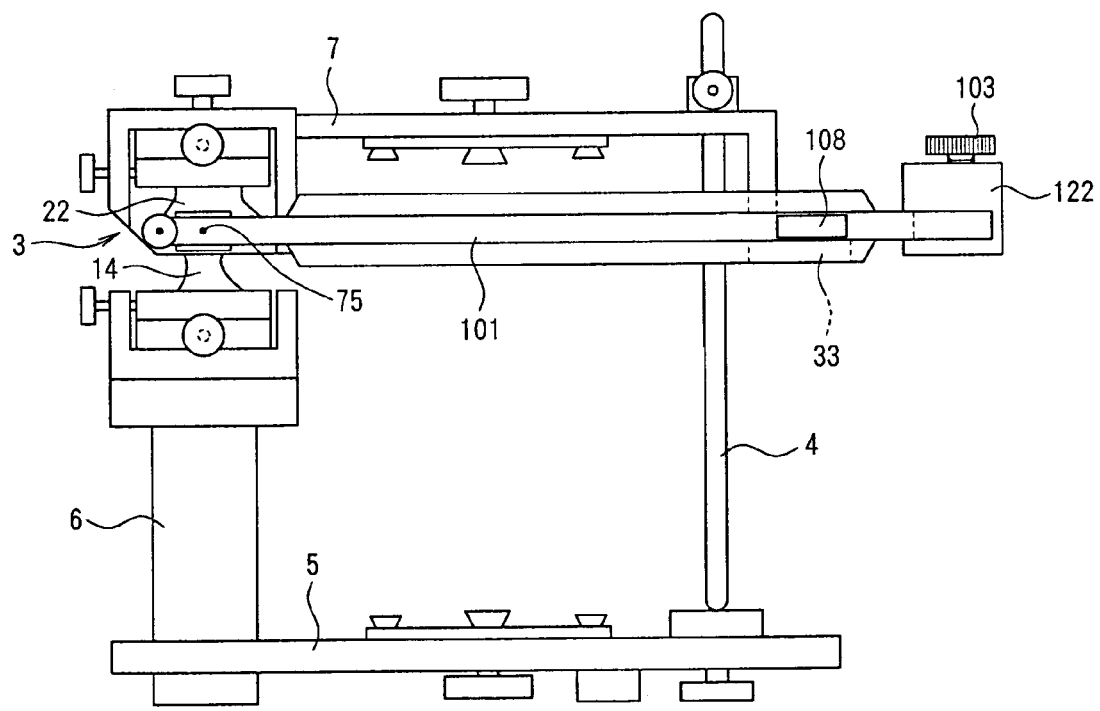
FIG. 36 is a side view showing an example of a connection to the occludator.

FIG. 36 shows that the face bow F is connected to the occludator.

In the present embodiment, two marking members 75 are disposed on the right and left so as to be arranged in the longitudinal direction. This is because the longitudinal direction (X-axis direction) is readily recognized.

Other configurations and operations/working effects are similar to those of the above-described embodiments.

In all the embodiments, the face bow F has the marking members 75 in order to obtain a reference for generating a solid model with stereolithography. Thus, even when the marking members 75 are not provided, a setting is correctly made on a standard plane (FH plane and so on) by the face bow F and an occlusion plane obtained by the correct standard plane can be copied to the occludator. Therefore, the face bow which can make a setting on the standard plane more positively and sample the occlusion plane is connected to the occludator of the present invention which can reproduce an articular movement closer to a temporomandibular joint of a patient, so that more prostheses or the like can be provided under occlusion conditions of the patient.

Moreover, the body of the face bow F is made of a radiolucent material in order to prevent the face bow F from causing problems during photographing. When no problem occurs, the face bow F does not have to be made of a radiolucent material.

Further, an elastic sheet having a thickness corresponding to a gap between the mandibular condyle and the maxillary fossa of the embodiments may be interposed between the mandibular condyle model and the maxillary fossa model which are mounted on the occludator. Further, a lubricant or the like may be applied to a contact surface between the mandibular condyle model and the maxillary fossa model to adjust sliding.

Figure 37:
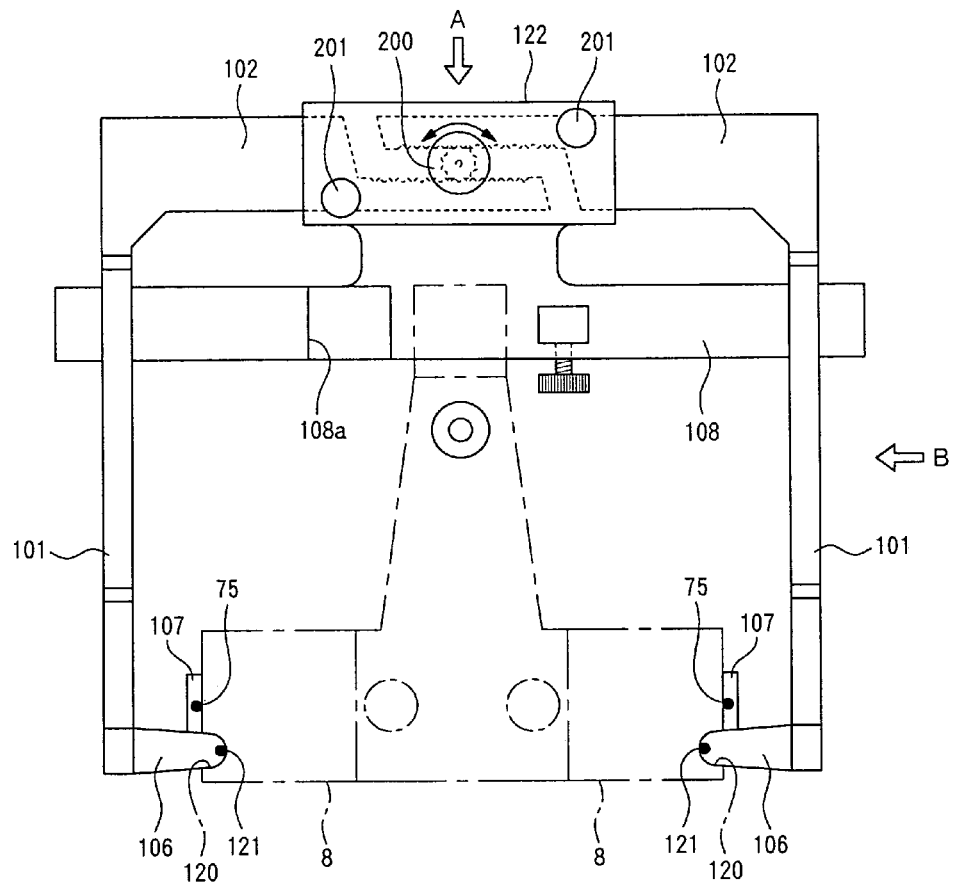
FIG. 37 is a plan view showing another example of a mechanism for adjusting a distance between right and left leg bodies.
Figure 38:
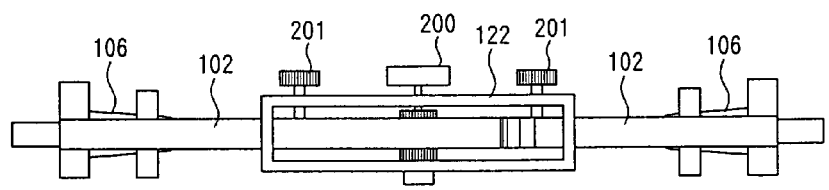
FIG. 38 is a front view showing another example of a mechanism for adjusting a distance between right and left leg bodies.

As shown in FIGS. 37 and 38, the following configuration is also applicable: a distance between the right and left legs is adjusted by a gear mechanism, and the right and left leg bodies 101 are equal in displacement in the lateral direction. Reference numeral 201 denotes a fixing screw. That is, the mechanism for adjusting a distance between the right and left legs is not limited to those of the embodiments. Moreover, the mechanism for positioning the nose piece is not limited to the above.

INDUSTRIAL APPLICABILITY

As described above, with the present invention, it is possible to fabricate a crown prosthesis and so on more suitably for a target person and achieve a more appropriate diagnosis, treatment and so on of occlusion.

The invention claimed is:

1. An occludator, comprising a lower bow-shaped part for mounting a lower jaw tooth mold, an upper bow-shaped part for mounting an upper jaw tooth mold, and
    right and left joints which enable a movement including an opening/closing movement and a lateral movement so that the lower bow-shaped part and the upper bow-shaped part are vertically brought into contact with each other via an elastic body for applying an urging force in a direction of bringing the lower bow-shaped part and the upper bow-shaped part relatively close to each other, characterized in that each of the right and left joints comprises
    an artificial condyle which is detachably mounted on the lower bow-shaped part and protrudes upward and an artificial articular fossa which is detachably mounted on the upper bow-shaped part and is opposed to the artificial condyle from above, the artificial condyle and the artificial articular fossa are both identical in contour to the mandibular condyle or the maxillary fossa protruding closer to an ideal model during fabrication of the upper jaw tooth model, wherein,
    each of the right and left joints is constituted of an upper joint and a lower joint which are opposed to each other, the upper joint is constituted of an upper mounting member supported by the upper bow-shaped part, a maxillary fossa model, and first mounting means for detachably mounting a pedestal of the maxillary fossa model on the upper mounting member, and the lower joint is constituted of a lower mounting member fixed on the lower bow-shaped part, a mandibular condyle model, and second mounting means for detachably mounting a pedestal of the mandibular condyle model on the lower mounting member, and wherein,
    the first mounting means is constituted of a male screw part formed on the upper mounting member, a cylindrical member having a female screw formed in an inner surface, the female screw enabling to be screwed to the male screw, and an inner flange which is formed integrally with the cylindrical member, forms a hole permitting passage of the maxillary fossa model, and can make contact with a periphery of the pedestal of the maxillary fossa model, and the periphery of the pedestal of the maxillary fossa model is sandwiched between the upper mounting member and the inner flange by screwing the female screw to the male screw.

2. The occludator according to claim 1, characterized in that the second mounting means is constituted of a male screw part formed on the lower mounting member, a cylindrical member having a female screw formed in an inner surface, the female screw enabling to be screwed to the male screw, and an inner flange which is formed integrally with the cylindrical member, forms a hole permitting passage of the mandibular condyle model, and can make contact with a periphery of the pedestal of the mandibular condyle model, and the periphery of a pedestal of the mandibular condyle model is sandwiched between the lower mounting member and the inner flange by screwing the female screw to the male screw.

3. The occludator according to claim 1, characterized in that the first mounting means comprises
a ring-shaped part which is formed on an end of the upper mounting member and has an inner concave part permitting insertion of the pedestal of the maxillary fossa model, and
a fixing screw which laterally penetrates the ring-shaped part while being connected to the ring-shaped part by screwing, and has an end screwed inside the pedestal from a part where the female screw is not formed on the side of the pedestal of the maxillary fossa model.

4. The occludator according to claim 3, characterized in that the pedestal in cross section and the concave part of the ring-shaped part are both polygonal, and the pedestal is so shaped as to be engaged with the concave part of the ring-shaped part.

5. The occludator according to claim 1, characterized in that the second mounting means comprises
a ring-shaped part which is formed on an end of the lower mounting member and has an inner concave part permitting insertion of the pedestal of the mandibular condyle model, and a fixing screw which laterally penetrates the ring-shaped part while being connected to the ring-shaped part by screwing, and has an end screwed inside the pedestal from a part where the female screw is not formed on a side of the mandibular condyle model.

6. The occludator according to claim 5, characterized in that the pedestal in cross section and the concave part of the ring-shaped part are both polygonal, and the pedestal is so shaped as to be engaged with the concave part of the ring-shaped part.

7. The occludator according to claim 1, characterized by further comprising position adjusting means for laterally adjusting a position of at least one of the artificial condyle and the artificial articular fossa.

8. The occludator according to claim 1, characterized by further comprising connecting parts on a pair of lateral positions in the occludator, the connecting parts connecting a face bow.

9. An occlusion confirming system, characterized in that the system comprises a CT device for photographing a temporomandibular joint of a target person, a stereolithography machine for forming a solid model of the temporomandibular joint, by determining consecutive two-dimensional sectional data along the Z axis from the three-dimensional image data when obtaining three-dimensional image data on a target temporomandibular joint from the X-ray CT device, performing photo-curing to obtain the two-dimensional contours of the two-dimensional sectional data, and repeatedly overlaying the contours, so that a resin solid model of a temporomandibular joint is fabricated, and an occludator including a lower bow-shaped part for mounting a lower jaw tooth mold, an upper bow-shaped part for mounting an upper jaw tooth mold, and right and left joints for connecting the lower bow-shaped part and the upper bow-shaped part, the joint comprises
an artificial condyle which is mounted on the lower bow-shaped part and protrudes upward and an artificial articular fossa which is mounted on the upper bow-shaped part and is opposed to the artificial condyle from above, the artificial condyle and the artificial articular fossa are each constituted of the solid model formed by the stereolithography machine, and the solid models of the artificial condyle and the artificial articular fossa are integrally formed.

10. The occlusion confirming system according to claim 9, characterized by further comprising an elastic body for applying an urging force in a direction of bringing the lower bow-shaped part and the upper bow-shaped part relatively close to each other.

11. The occlusion confirming system according to 9, characterized in that each of the right and left joints is constituted of an upper joint and a lower joint which are opposed to each other,
the upper joint is constituted of an upper mounting member supported by the upper bow-shaped part, a maxillary fossa model, and first mounting means for detachably mounting a pedestal of the maxillary fossa model on the upper mounting member, and
the lower joint is constituted of a lower mounting member fixed on the lower bow-shaped part, a mandibular condyle model, and second mounting means for detachably mounting a pedestal of the mandibular condyle model on the lower mounting member.

12. The occlusion confirming system according to claim 11, characterized in that the first mounting means is constituted of a male screw part formed on the upper mounting member,
a cylindrical member having a female screw formed in an inner surface, the female screw capable of being screwed to the male screw, and
an inner flange which is formed integrally with the cylindrical member, forms a hole permitting passage of the maxillary fossa model, and can make contact with a periphery of a pedestal of the maxillary fossa model, and the periphery of the pedestal of the maxillary fossa model is sandwiched between the upper mounting member and the inner flange by screwing the female screw to the male screw.

13. The occlusion confirming system according to claim 11, characterized in that the second mounting means is constituted of a male screw part formed on the lower mounting member, a cylindrical member having a female screw formed in an inner surface, the female screw enabling to be screwed to the male screw, and an inner flange which is formed integrally with the cylindrical member, forms a hole permitting passage of the mandibular condyle model, and can make contact with the periphery of a pedestal of the mandibular condyle model, and the periphery of the pedestal of the mandibular condyle model is sandwiched between the lower mounting member and the inner flange by screwing the female screw to the male screw.

14. The occlusion confirming system according to claim 13, characterized in that the first mounting means comprises a ring-shaped part which is formed on an end of an upper mounting member and has an inner concave part permitting insertion of the pedestal of the maxillary fossa model, and a fixing screw which can laterally penetrate the ring-shaped part while being connected to the ring-shaped part by screwing, and has an end capable of being screwed inward or in contact with a side of the pedestal of the maxillary fossa model.

15. The occlusion confirming system according to claim 11, characterized in that the second mounting means comprises
a ring-shaped part which is formed on an end of the lower mounting member and has an inner concave part permitting insertion of the pedestal of the mandibular condyle model, and
a fixing screw which can laterally penetrate the ring-shaped part while being connected to the ring-shaped part by screwing, and has an end capable of being screwed inward or in contact with a side of the pedestal of the mandibular condyle model.

16. The occlusion confirming system according to claims 11, characterized by further comprising upper positioning means for regulating a position of the pedestal of the maxillary fossa model relative to a upper mounting part.

17. The occlusion confirming system according to claim 11, characterized by further comprising lower positioning means for regulating a position of the pedestal of the mandibular condyle model relative to a lower mounting part.

18. The occlusion confirming system according to claim 9, characterized by further comprising position adjusting means for laterally adjusting a position of at least one of the artificial condyle and the artificial articular fossa.

19. The occlusion confirming system according to claim 9, characterized by further comprising
a face bow including a face bow body which is used for reproducing a positional relationship between the temporomandibular joint and
an occlusion plane on the occludator and has a pair of right and left legs stretching symmetrically, characterized in that at least the right and left legs are made of a material permitting passage of a light beam used in the CT device, and at least one marking member is provided on an end of each of the right and left legs, the marking member being made of a material not permitting the passage of the light beam.

20. The occlusion confirming system according to claim 19, characterized in that the face bow comprises a nose piece which is supported by the face bow body and brought into contact with a hollow in an upper part of a nose of a patient, and the nose piece comprises a position adjusting mechanism capable of adjusting a position at least in a vertical direction and a longitudinal direction with respect to the face bow body.

21. The occlusion confirming system according to claim 19, characterized in that the face bow body comprises a level.

22. The occlusion confirming system according to claim 19, characterized in that the marking member is disposed on a position presumed to be laterally opposed to a center of the mandibular condyle of a patient.

23. The occlusion confirming system according to claim 19, characterized by further comprising an ear rod on an end of the leg in the face bow, the ear rod being inserted into an external auditory meatus of a patient, and each of right and left sides of the occludator has an insertion hole for insertion of the ear rod.

24. The occlusion confirming system according to 19, comprising a headgear fixed on a head of a target person, characterized in that the head gear comprises right and left connecting parts for temporarily connecting right and left ends of the face bow and connection position adjusting means for adjusting a position of the connecting part to a predetermined position.

25. The occlusion confirming system according to claim 24, characterized in that the headgear comprises fixing means for temporarily fixing the headgear to the CT device.

26. An occlusion confirming system characterized in that the system comprises
a CT device for photographing a temporomandibular joint of a target person,
a stereolithography machine for forming a solid model of the temporomandibular joint on a basis of three-dimensional image data of the temporomandibular joint specified by image information photographed by the CT device,
an occludator including a lower bow-shaped part for mounting a lower jaw tooth mold, and
an upper bow-shaped part for mounting an upper jaw tooth mold, and right and left joints for connecting the lower bow-shaped part and the upper bow-shaped part,
each of the right and left joints comprises an artificial condyle which is mounted on the lower bow-shaped part and protrudes upward and an artificial articular fossa which is mounted on the upper bow-shaped part and is opposed to the artificial condyle from above, and at least one of the artificial condyle and the artificial articular fossa is constituted of the solid model formed by the stereolithography machine, and
a database for storing ideal model information about a temporomandibular joint condyle,
characterized in that the system further comprises data correcting means for correcting three-dimensional data on the temporomandibular joint condyle specified by image information photographed by the CT device such that a contour of the temporomandibular joint condyle specified by the image information photographed by the CT device is identical to a contour protruding closer to an ideal model, when a comparison is made between the coutour of the temporomandibular joint condyle specified by the image information photographed by the CT device and the corresponding ideal model on the database and it is decided that the temporomandibular joint condyle wears more than a predetermined degree.

* * * * *